(12) United States Patent
Descour et al.

(10) Patent No.: US 7,492,535 B2
(45) Date of Patent: Feb. 17, 2009

(54) MULTIMODAL MINIATURE MICROSCOPE

(75) Inventors: Michael Descour, Tucson, AZ (US); Russell Dupuis, Austin, TX (US); Eric Anslyn, Austin, TX (US); Rebecca Richards-Kortum, Austin, TX (US)

(73) Assignees: Board of Regents, The University of Texas System, Austin, TX (US); Arizona Board of Regents on Behalf of The University of Arizona, Tucson, AZ (US)

( * ) Notice: Subject to any disclaimer, the term of this patent is extended or adjusted under 35 U.S.C. 154(b) by 503 days.

(21) Appl. No.: 11/108,616

(22) Filed: Apr. 18, 2005

(65) Prior Publication Data

US 2006/0058611 A1 Mar. 16, 2006

Related U.S. Application Data

(63) Continuation of application No. 10/237,151, filed on Sep. 6, 2002, now abandoned.

(60) Provisional application No. 60/318,059, filed on Sep. 7, 2001.

(51) Int. Cl.
*B02B 7/02* (2006.01)
(52) U.S. Cl. .................. 359/818; 359/381; 359/819; 359/821; 382/284
(58) Field of Classification Search ................ 359/811, 359/818, 819, 821, 827, 368, 381, 382, 390, 359/391; 82/128, 284
See application file for complete search history.

(56) References Cited

U.S. PATENT DOCUMENTS

| 5,042,889 | A | 8/1991 | Benzoni ...................... 385/16 |
| 5,119,852 | A | 6/1992 | von Benda .................... 141/32 |
| 5,501,893 | A | 3/1996 | Laermer et al. ............. 428/161 |
| 5,633,752 | A | 5/1997 | Tsuchiya et al. ............. 359/390 |
| 5,719,700 | A | 2/1998 | Corcuff et al. .............. 359/368 |
| 6,094,299 | A | 7/2000 | Schau et al. ................. 359/383 |
| 6,263,233 | B1 | 7/2001 | Zavislan et al. ............. 600/476 |
| 6,466,381 | B2 | 10/2002 | Engelhardt ................... 359/804 |
| 2003/0151742 | A1* | 8/2003 | Silvermintz et al. ......... 356/318 |
| 2004/0101210 | A1* | 5/2004 | Weinstein et al. ........... 382/284 |

OTHER PUBLICATIONS

Äyräs et al., "Multilevel structures in sol-gel thin films with a single UV-exposure using a gray-scale mask," *Thin Solid Films*, 352:9-12, 1999.
Descour et al., "Toward the development of miniaturized imaging systems for detection of pre-cancer," *IEEE Journal of Quantum Electronics*, 38(2):122-130, 2002.
Rantala et al., "Binary phase zone-plate arrays based on hybrid sol-gel glass," *Optics Letters*, 23:1939-1941, 1998.

(Continued)

*Primary Examiner*—Huy K Mai
(74) *Attorney, Agent, or Firm*—Fulbright & Jaworski L.L.P.

(57) ABSTRACT

Apparatus for receiving and positioning optical components. The apparatus includes a substrate, one or more mounting slots, and one or more springs. The one or more mounting slots are formed in the substrate, and each mounting slot includes a mounting slot wall. At least one of the mounting slots is adapted to receive an optical component. At least one of the mounting slots is coupled to one of the springs.

17 Claims, 15 Drawing Sheets

OTHER PUBLICATIONS

Rantala et al., "Direct UV patterning of thick hybrid glass films for micro-opto-mechanical structures," *Electronics Letters*, 36(6):530-531, 2000.

Wilson and Beck, "Fracture testing of bulk silicon microcantilever beams subjected to a side load", *Journal of Microelectromechanical Systems*, 5(3):142-150, 1996.

* cited by examiner

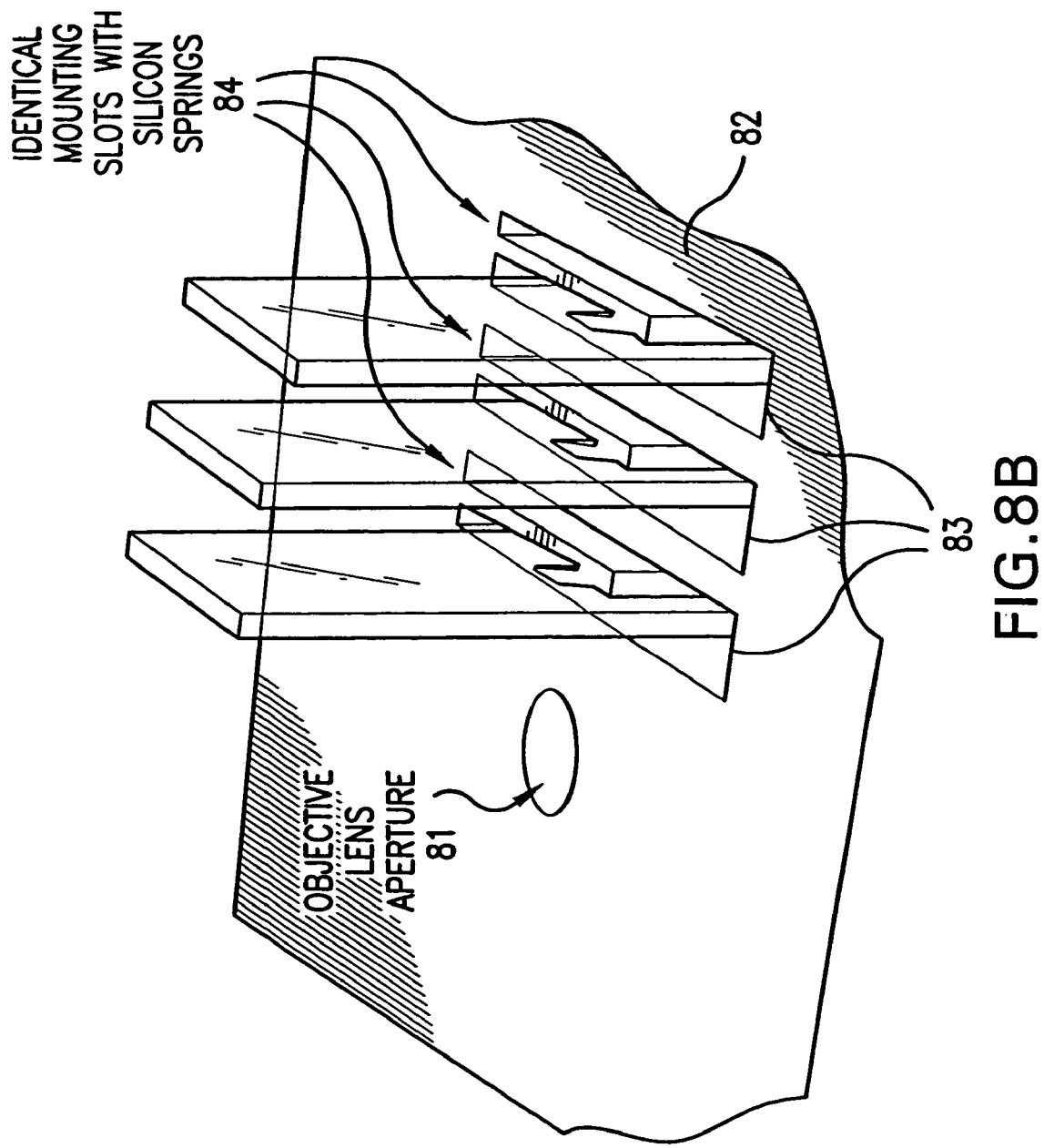

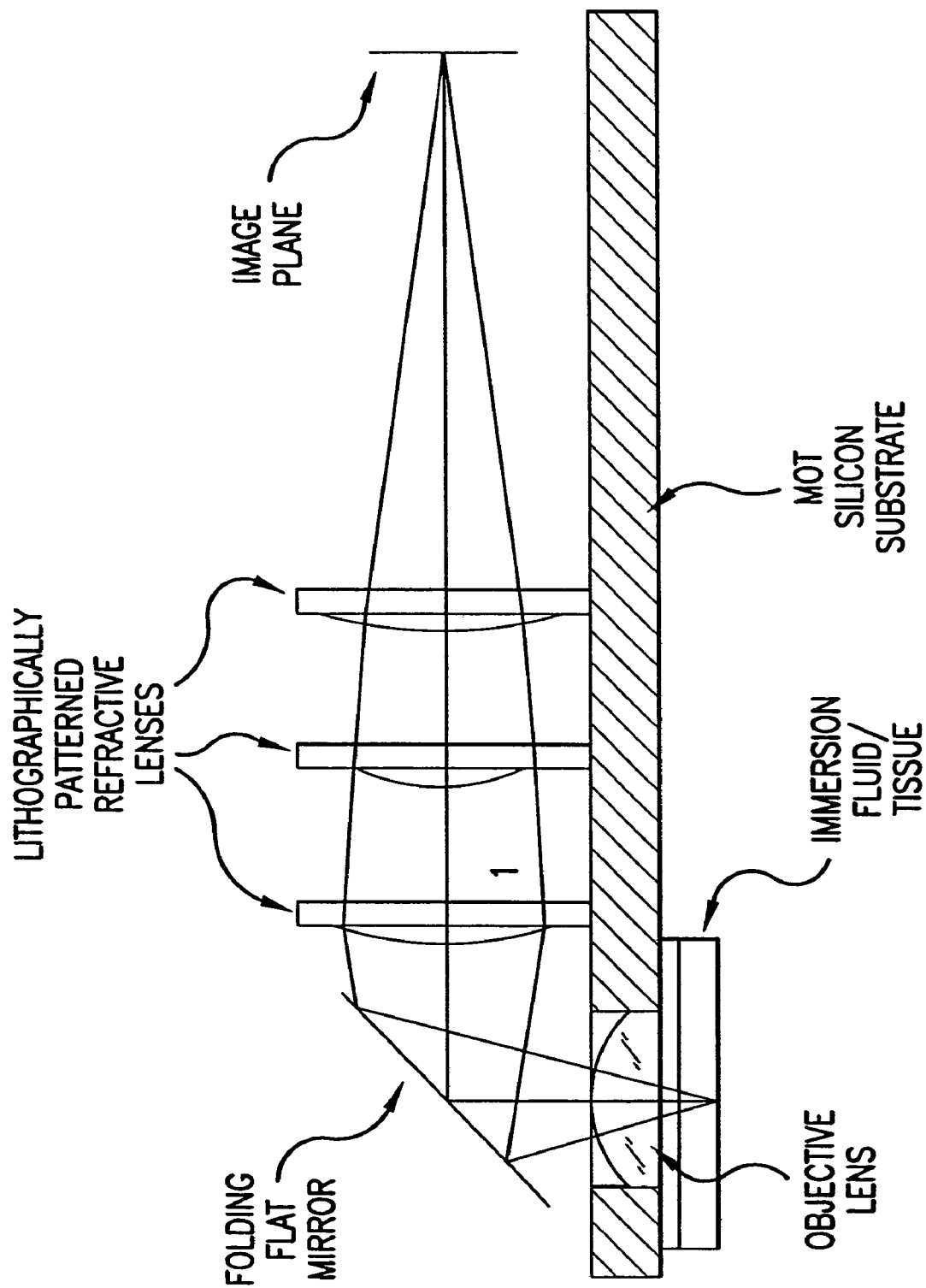

MULTIMODAL MINIATURE MICROSCOPE

This is a continuation application of U.S. patent application Ser. No. 10/237,151 filed on Sep. 6, 2002, now abandoned which claims priority to provisional U.S. Patent Application No. 60/318,059 entitled "Multimodal Miniature Microscope," which was filed on Sep. 7, 2001. The above-referenced disclosures are incorporated by reference.

This invention was made with government support under grant Nos. NSF BES-0086736 and NSF SGER ECS-0074578 awarded by the National Science Foundation. The government has certain rights in the invention.

BACKGROUND OF THE INVENTION

1. Field of the Invention

The present invention relates generally to the field of diagnostic imaging. More particularly, it concerns a microscope that utilizes the interaction of light with tissues in many modalities to image morphology and biochemistry, thereby providing better delineation of tumors. Even more particularly, it concerns a miniaturized microscope capable of different imaging modalities such as optical sectioning, 3-D spectral fluorescence imaging, and reflectance imaging.

2. Description of Related Art

The American Cancer Society estimates that 1,220,100 people will have been diagnosed with cancer in 2000. In the same year, 552,200 persons were expected to succumb to cancer. Despite significant advances in treatment, early detection of cancer and its curable precursors remains the best way to ensure patient survival and quality of life.

Pre-cancers are characterized by morphologic and biochemical changes that include increased nuclear size, increased nuclear to cytoplasmic ratio, hyperchromasia, pleomorphism, angiogenesis, and increased metabolic rate. These changes currently can only be assessed through invasive biopsy. Early detection of curable pre-cancers has the potential to significantly lower cancer mortality and morbidity. Many visual exam procedures, such as colonoscopy and bronchoscopy, are routinely used to identify pre-malignant changes and early cancers. However, these techniques do not assess the microscopic and/or biochemical changes which are the hallmark of pre-cancer. Thus, these techniques' sensitivity and specificity are limited.

Early detection would be particularly beneficial in the treatment of several types of cancers. For instance, cancer of the oral cavity is usually not diagnosed until it is in an advanced stage. In the advanced stage, treatment is more disfiguring, expensive, and prone to failure. Thus, early detection of pre-cancer is the best method to improve patient quality of life and survival. Certain lesions in the oral cavity have been identified clinically to have the potential for malignant conversion. These include leukoplakia (white plaques) and erythroplakia (velvety, reddish lesions). Invasive biopsies are often required to confirm the presence of pre-cancer. Thus, despite the easy accessibility of the oral cavity to examination, there is no satisfactory mechanism to adequately screen and detect pre-cancers. The development of a noninvasive and accurate method for real-time screening and diagnosis of oral cavity lesions would have great potential to improve early detection of neoplastic changes, and thereby improve the quality of life and survival rates for persons developing carcinomas of the oral cavity.

Cervical cancer is the third most common cancer in women worldwide and the leading cause of cancer mortality in women in developing countries. The curable precursor to cervical cancer is cervical intra-epithelial neoplasia. In the U.S. over $6 billion are spent annually in the evaluation and treatment of low-grade precursor lesions. Approximately 50 million Pap smears are performed annually in the U.S. to screen for cervical cancer and its precursor. The National Cancer Institute estimates 6-7% of these tests to be abnormal. However, cervical cancer goes undetected in developing countries because of the cost of the tests and the lack of trained personnel and resources. In the U.S., resources are wasted on the evaluation and treatment of lesions that are not likely to progress to cancer.

Optical technologies offer the ability to image tissue with unprecedented spatial and temporal resolution using low-cost, portable devices. As such, optical technologies represent an ideal approach to imaging early neoplasia. Multiple in vivo optical imaging and spectroscopic modalities have been explored recently as diagnostic tools in medicine. These modalities include multi-spectral fluorescence imaging, multi-spectral reflectance imaging with unpolarized and polarized light, confocal microscopy, reflectance, and fluorescence spectroscopy. In the ultraviolet (UV) and visible regions of the spectrum, tissue reflectance spectra provide information about the wavelength dependent scattering of tissue as well as electronic absorption bands, primarily those of oxy- and deoxyhemoglobin. The most common naturally occurring fluorophores include the aromatic amino acids, the co-factors NAD(P)H and FAD, crosslinks associated with collagen and elastin, and porphyrins.

Furthermore, optical technologies may be used to complement existing pre-cancer treatments, such as chemoprevention. Chemoprevention refers to the use of chemical agents to prevent or to delay the development of cancer in healthy populations or patients with precancerous tissue changes. Despite their promise, chemoprevention studies have several inherent problems. One is that many patients hesitate to enroll in such trials because they require multiple biopsies throughout the period when the chemopreventive agent is given. Biopsies are processed to measure morphologic and biochemical changes associated with cancer progression and assess drug response. A second problem is that the biopsy process itself can interrupt the natural progression of the lesion. Many times these lesions are small enough that the biopsy is the cure; frequent biopsies make it difficult to accurately assess drug response. Thus, tools that non-destructively assess quantitative morphologic and biochemical changes that do not require biopsy could considerably improve chemoprevention studies.

Both screening and detection could be vastly improved by in vivo optical imaging technologies that improve the ability to recognize and delineate pre-cancerous lesions in the cervix with high sensitivity and specificity. A major challenge in implementing quantitative optical tools for widespread screening is to develop small, inexpensive imaging systems that provide both high sensitivity and high specificity for the biochemical and morphologic features of pre-cancer. A need therefore exists for small, inexpensive imaging systems that may enhance or replace traditional visual exam procedures to allow for more accurate identification of pre-cancerous lesions.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A shows a micro-optical element patterned in hybrid sol-gel material on a 150 micron thick glass substrate. FIG. 4B shows a hybrid sol-gel material patterned to a depth of 34 microns.

FIG. 5A shows the optical elements as seen under a microscope. FIG. 5B shows the optical elements observed in an SEM.

FIG. 6A shows the optical element in its penultimate position. FIG. 6B shows an image of a fabricated silicon spring that retains an optical element in the mounting slot. The width of the slot shown is 600 μm, and the length is 4,000 μm.

FIGS. 8A, 8B, and 8C show various aspects of one embodiment of the device of the present invention. FIG. 8A shows a device that contains only refractive microlenses and a folding mirror. FIG. 8B shows a fabricated MOT silicon substrate comprising silicon-spring mounting slots. FIG. 8C shows three 150-micron thick, unpatterned glass substrates mounted in the MOT. The plates are separated by 800 microns.

FIG. 9 shows one design of a device that operates in the red wavelength region.

DESCRIPTION OF ILLUSTRATIVE EMBODIMENTS

In one embodiment, the present invention is directed to a class of microscopes, and in particular miniature microscopes, that utilize the interaction of light with tissues in many modalities to image morphology and biochemistry in vivo, yielding tools that provide better delineation of tumors. It is contemplated that the devices of the present invention may image microscopic and molecular features of pre-cancer. The proposed miniature microscopes are multi-modal because of their potential for enabling different imaging modalities, which may include optical sectioning, 3-D spectral fluorescence imaging, and reflectance imaging. The microscopes may be miniaturized by using a zero-alignment microscopic optical-system. Specifically, a micro-optical table ("MOT") substrate may be used. Various mounting slots may be formed in the MOT, and the mounting slots may be configured to receive and secure various optical components.

The size and cost of these microscopes can be eventually small enough so that they can aid in, for instance, guiding diagnostic biopsy and to aid in margin detection during tumor resection. The devices may have broad applicability in many organ sites due to their very compact size and capability for imaging. It has been previously demonstrated that the morphologic and biochemical changes that accompany pre-cancer can be probed using reflectance and fluorescence. Accordingly, the imaging devices of the present invention may be designed to image both reflected light and autofluorescence.

The multi-modal miniature microscopes proposed here represent a fundamentally new way of approaching pre-cancer detection. In one embodiment, the present devices integrate micro-optical systems, micro-mechanical components, and image sensors to achieve a high level of sensitivity and specificity in a miniaturized, cost-effective package.

Micro-Optical Tables

In order to provide for the miniaturization of microscopes in an effective manner, it is desirable to have a simple and accurate method of building optical systems. A novel method of constructing compact, three-dimensional imaging systems that consist of various optical elements that may include, for example, lenses and mirrors, micro-mechanical components, photo-detectors, and light sources is disclosed.

Figure 1:
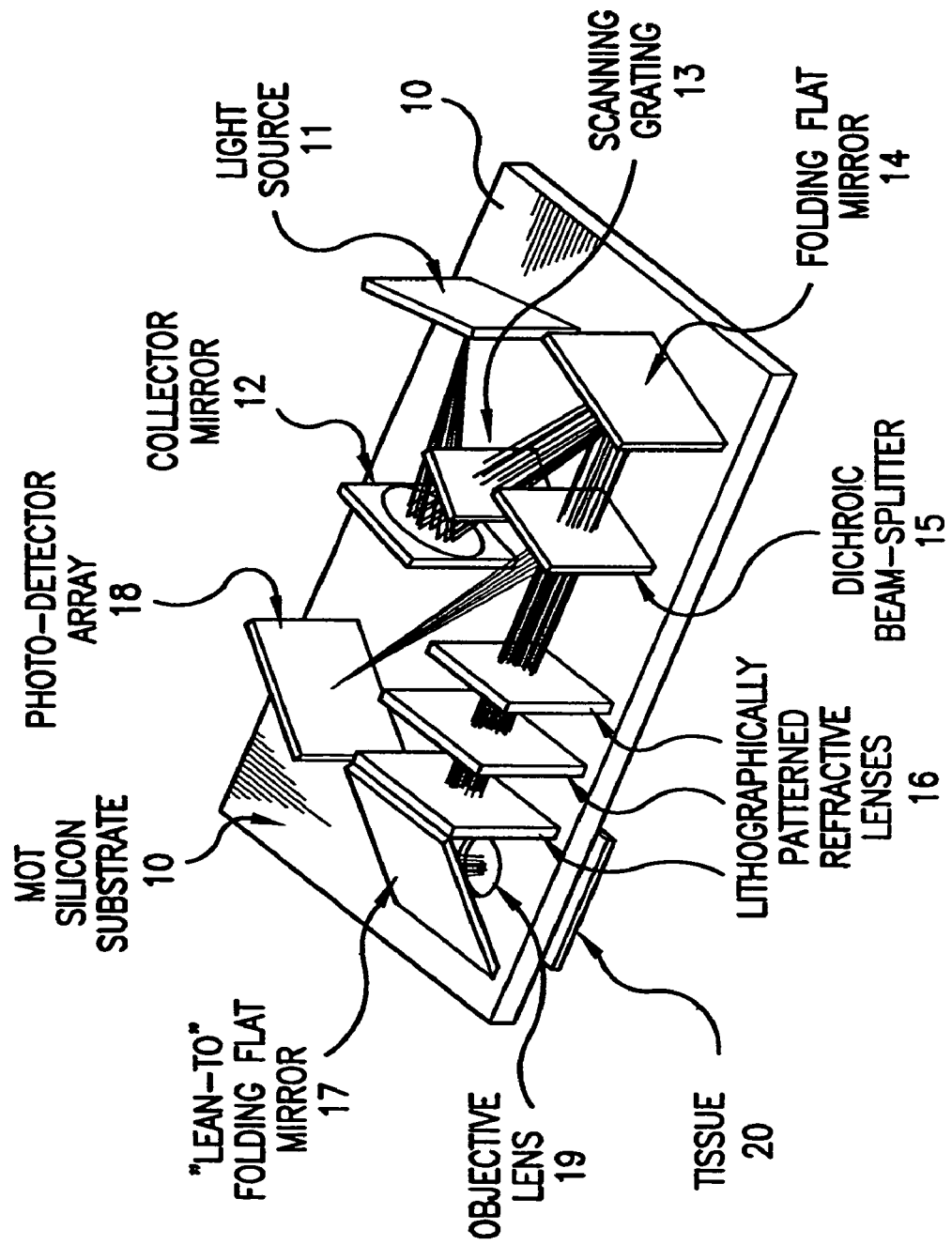
FIG. 1 shows a schematic of an optical-sectioning multi-modal miniature microscope device according to one embodiment of the present disclosure.

These optical elements, both active and passive, may be mounted on specially prepared MOT substrates, as shown in FIG. 1. The substrates are referred to as micro-optical tables, in analogy with the macroscopic version routinely used in optics laboratories. Preferably, the MOTs are made of silicon, although those skilled in the art will realize that other materials may also be used, such as metal. The MOT is a zero-alignment microscopic optical-system concept. In practical terms, the zero-alignment concept translates into assembly errors that are preferably smaller than the tolerances on the performance of the optical system.

Various mounting slots are formed in the MOT. The mounting slots may be formed in a variety of ways, such as through conventional etching techniques. The accurate positioning of each mounting slot relative to other mounting slots on the MOT may be obtained by using a sub-micron-precision layout of the photomask from which the MOT may be made. The mounting slots may be etched into the MOTs to various depths. In one embodiment, the mounting slots may extend all the way through the MOT.

Figure 2A:
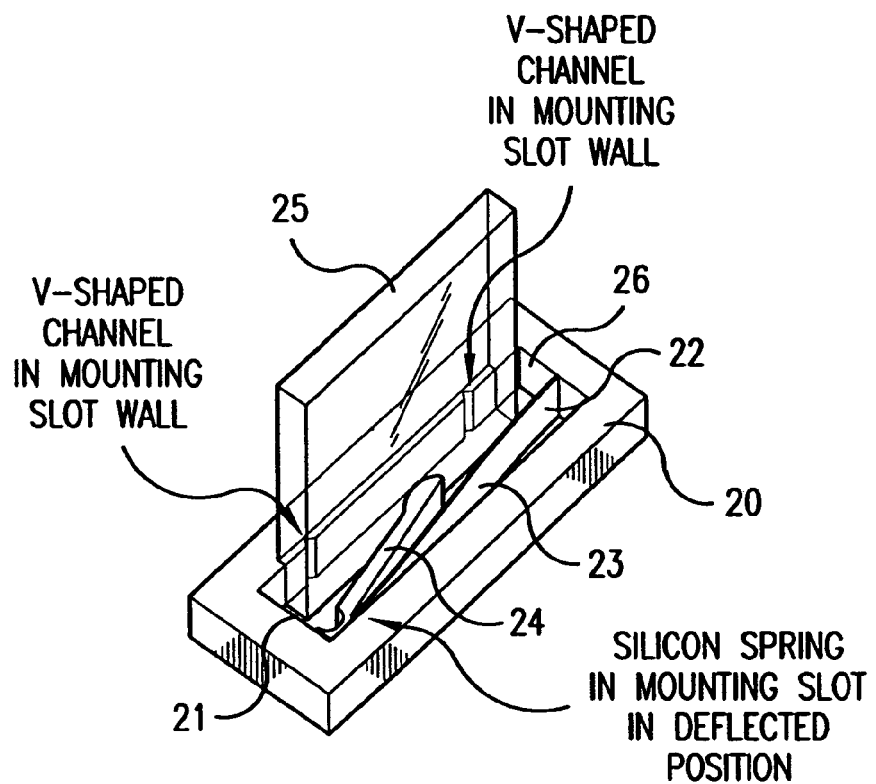
FIGS. 2A and 2B shows a detailed schematic view of an optical element mounted in a mounting slot etched in a silicon micro-optical table ("MOT") substrate according to one embodiment of the present disclosure.
Figure 2B:
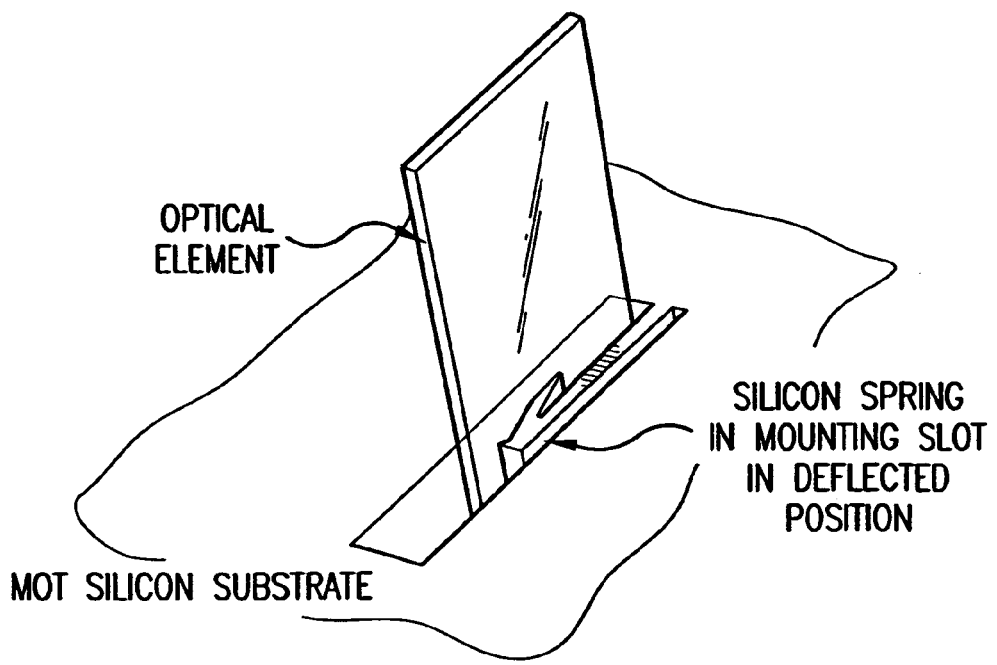

Preferably, each MOT also contains a spring device that serves to hold an optical element in place once it has been inserted into the MOT. A preferred embodiment of the mounting slot 21 formed in a MOT 20 and a spring 22 is shown in FIGS. 2A and 2B. In the embodiment shown in FIGS. 2A and 2B, the spring 22 has a first elongated portion 23 and a second shorter portion 24 that forms an angle with the first elongated portion. One of the purposes of the spring is to press-fit the optical component 25 into a more accurate position than might be achieved by using a simple slot alone. When an optical component 25 is inserted into the mounting slot 21, the spring 22 presses against the optical component and helps to position and secure the optical component in the mounting slot.

FIGS. 2A and 2B, illustrate an optical component inserted in a mounting slot. The insertion of the optical component causes the spring to be moved to a deflected position. The spring presses against the optical component, thereby helping to secure it in the mounting slot. FIG. 8B shows mounting slots 83 in which no optical components have been inserted.

Figure 8A:
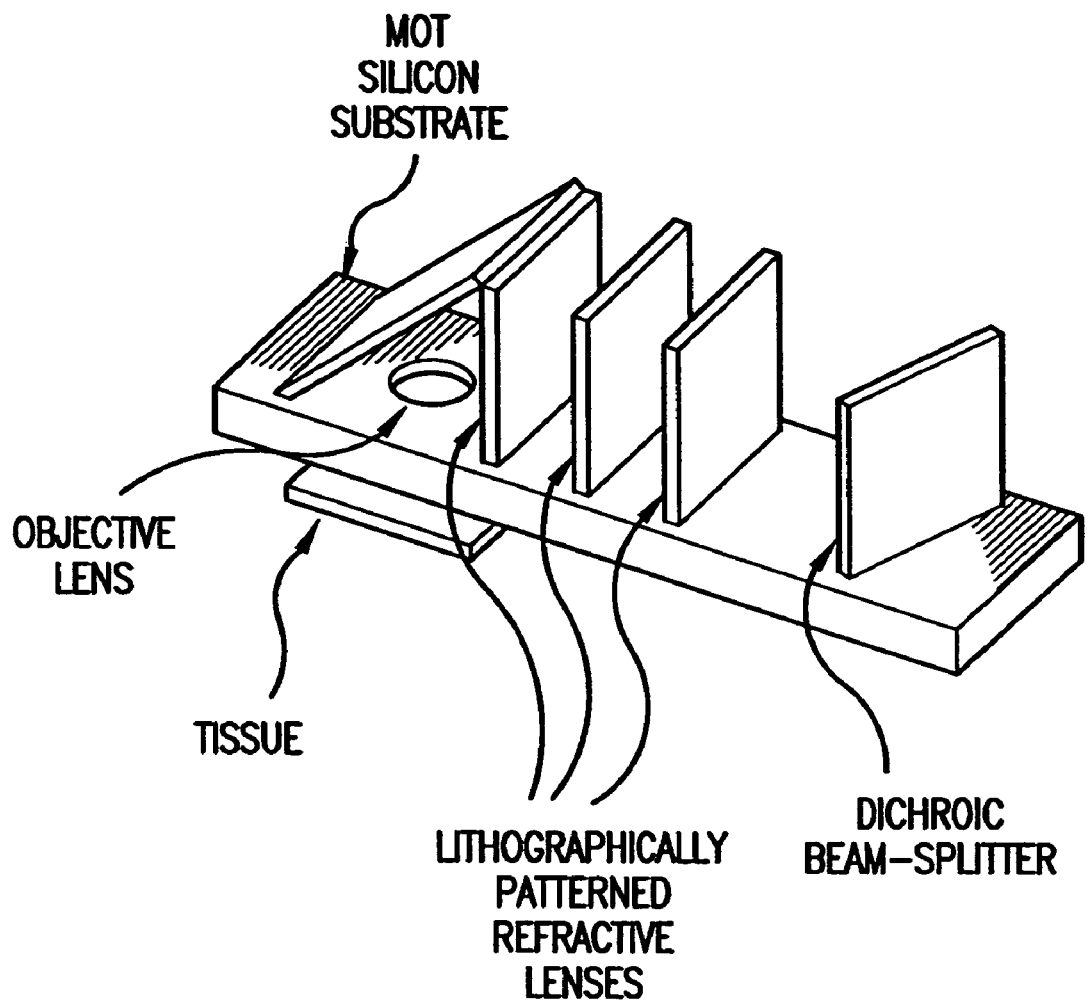
Figure 8C:
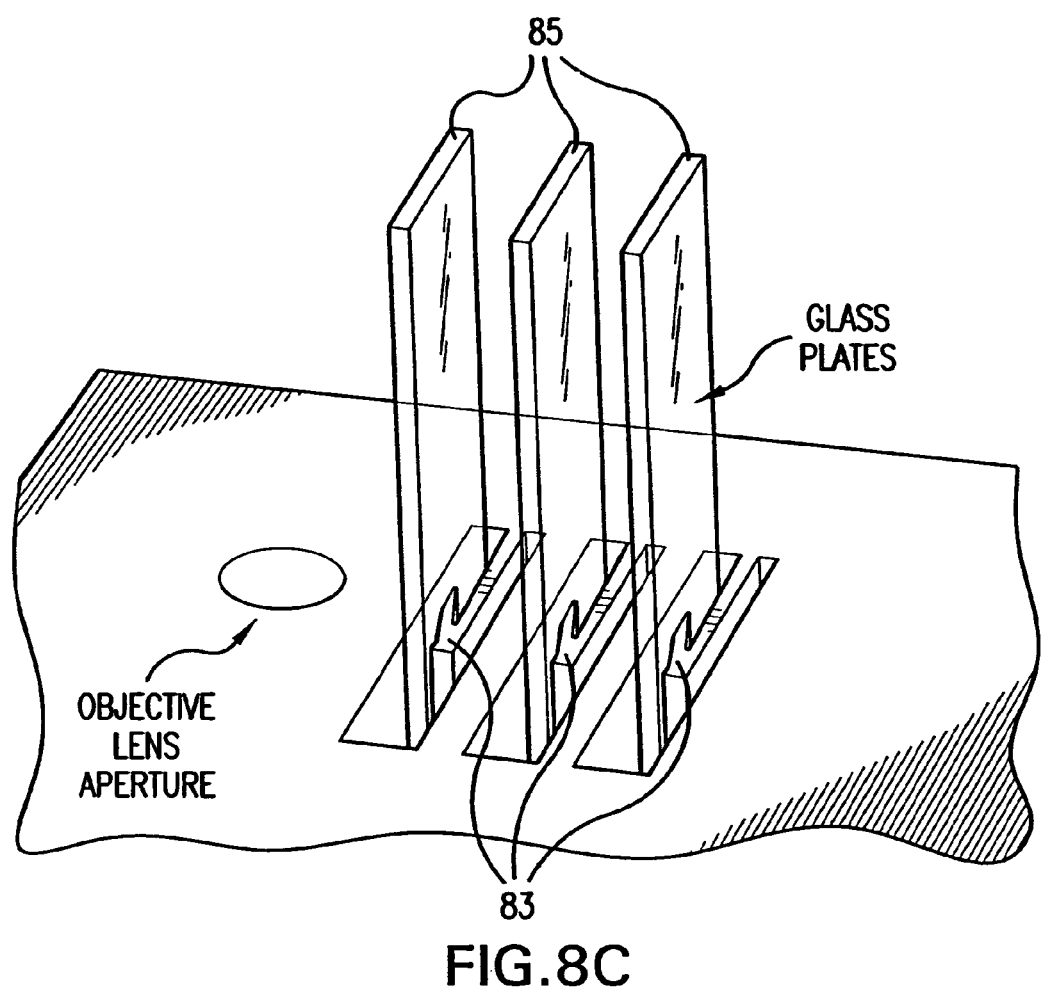

As no optical component has been inserted into the mounting slots 83, the springs 84 in FIG. 8B are not in a deflected position. FIG. 8C shows optical components 85 inserted into the mounting slots 83.

Figure 6A:
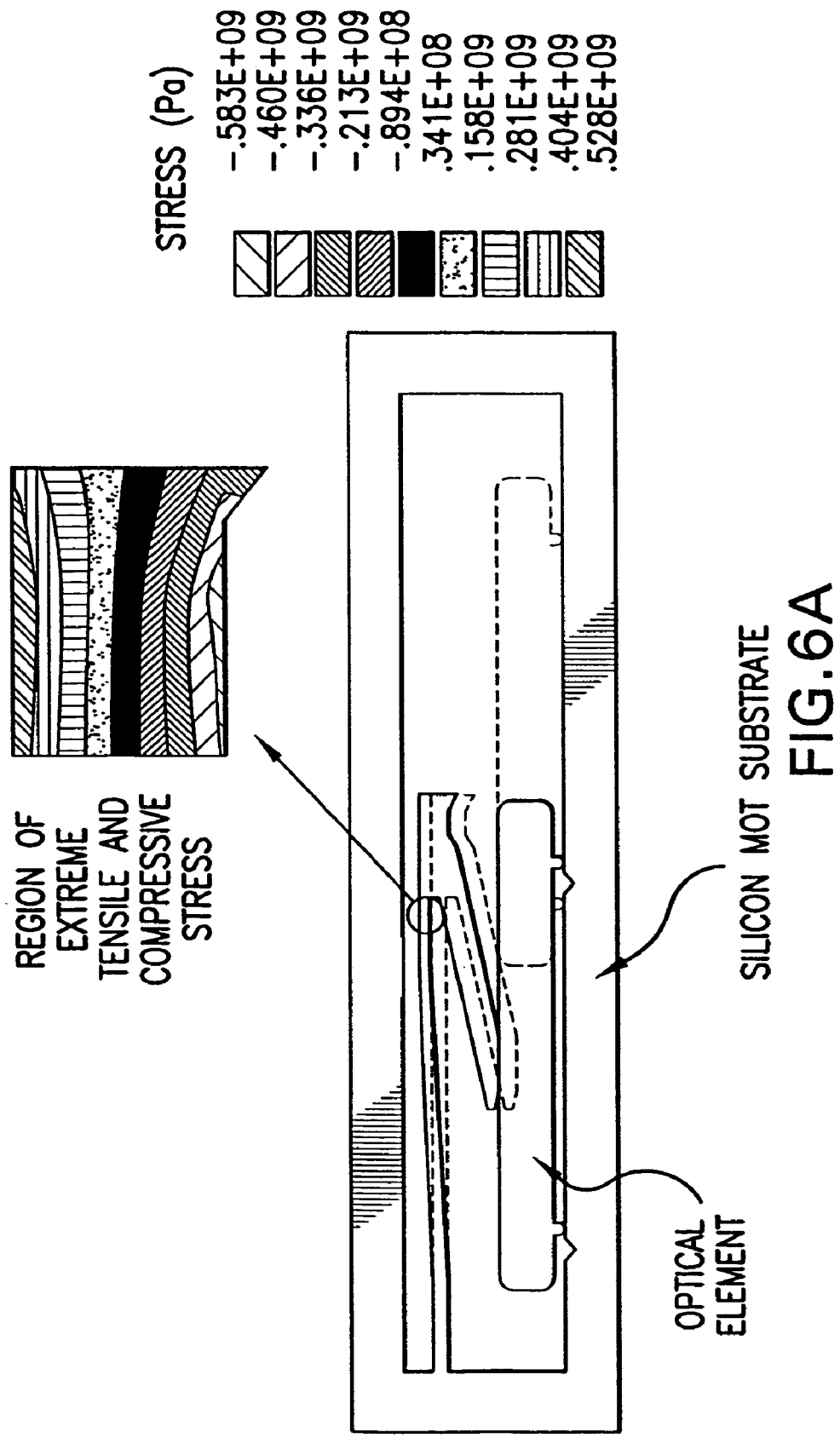
FIGS. 6A and 6B show silicon-spring displacement and the normal stress in the horizontal direction.
Figure 6B:
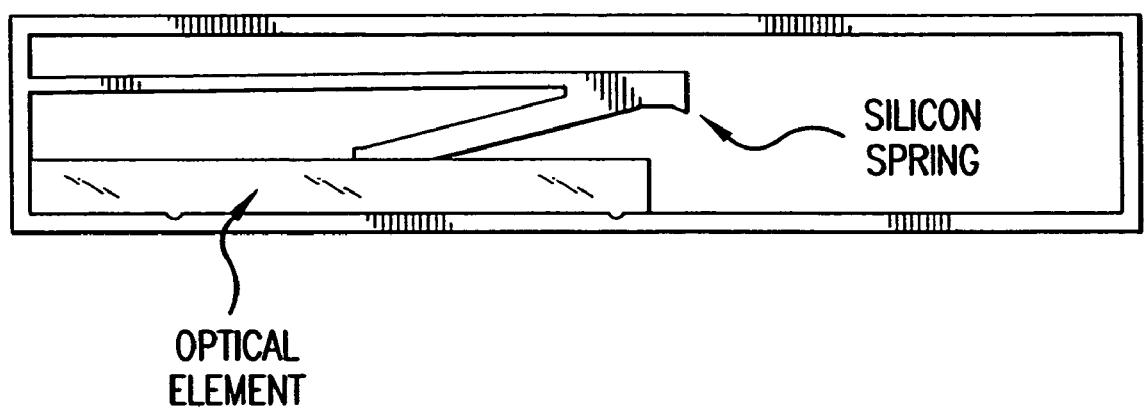

The shape of the spring shown in FIG. 2 was selected in part by generating a two-dimensional finite-element model to determine the displacement and stress fields in the silicon spring and the optical element as the optical element is inserted into the mounting slot. FIGS. 6A and 6B show the top view of a rectangular segment of a silicon MOT substrate. Also shown in FIG. 6, the silicon spring and an optical element are being positioned in the mounting slot. The dashed outlines in FIG. 6 indicate the starting positions of the silicon spring and the optical element. The filled outlines in FIG. 6 indicate positions of the silicon spring and the optical element that correspond to the maximum stresses in the silicon spring.

The objective of the analysis was to develop a silicon-spring design that would not fail during insertion of an optical element into a mounting slot. The spring design shown in FIG. 6A satisfies this criteria. Those skilled in the art will realize that several methods may be used to select other acceptable shapes for the spring.

The spring may be attached to the mounting slot in various ways. As shown in FIGS. 2A and 2B, a preferred embodiment is to attach the spring 22 to the mounting slot 21 at one point along the interior wall 26 of the mounting slot 21. It will be apparent to those skilled in the art that the spring may be attached to the mounting slot in variety of ways, including attaching the spring to multiple points within the mounting slot, or attaching the spring to the surface of the MOT. As used herein, the term "spring" is intended to refer to any component having a configuration suitable to assist in securing an optical component in the mounting slot. As previously stated, those skilled in the art will realize that there are many suitable configurations for the spring. Preferably, the spring is made of silicon, although those skilled in the art will realize that the spring may be made of other suitable materials.

Figure 10A:
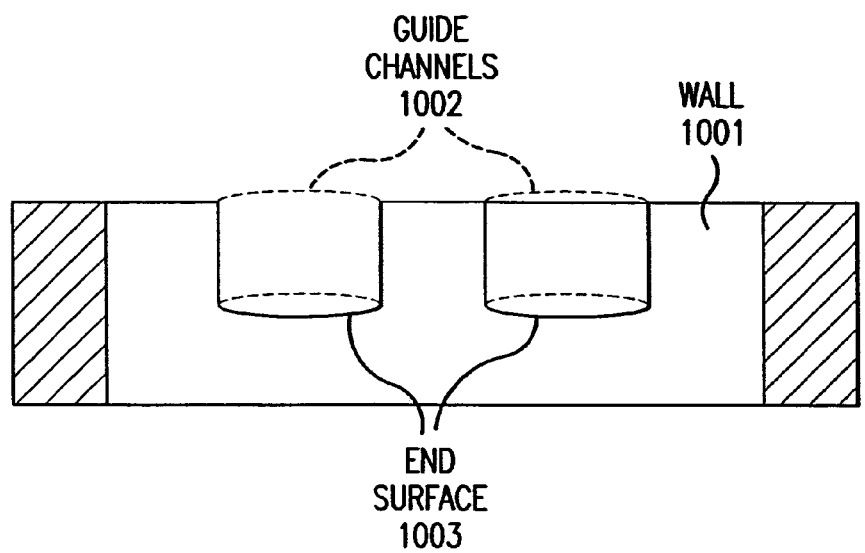
FIG. 10A shows a cross-section of an interior wall of a mounting slot, and two guide channels located on the wall.
Figure 10B:
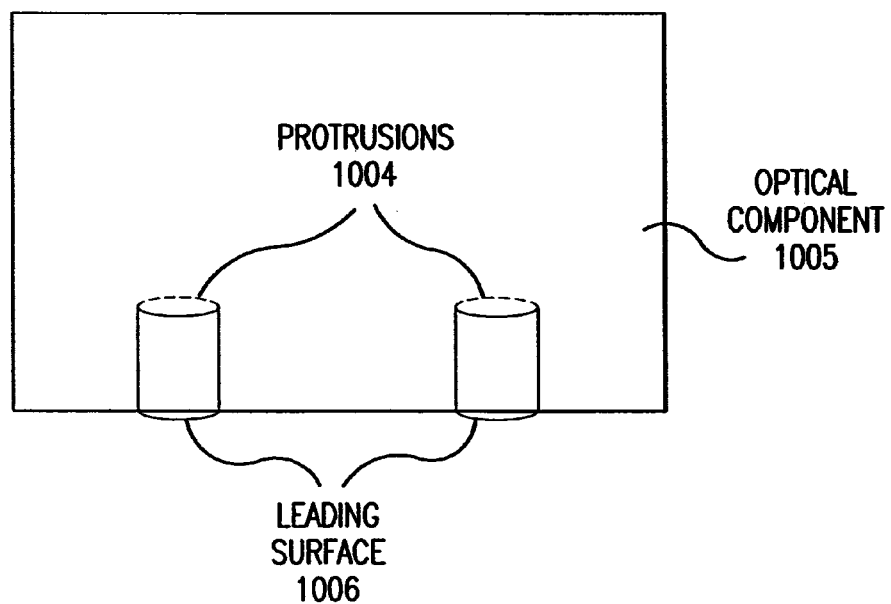
FIG. 10B shows a one side of an optical component, and two protrusions on the optical component.

Each mounting slot may also contain one or more guide channels that are formed in one or more of the walls of the mounting slot. FIG. 10A depicts one of the walls 1001 of a mounting slot, and two guide channels 1002 that are formed in the wall 1001. The guide channels may be a variety of shapes, including, for instance, cylindrical, "v" shaped, or rectangular. The guide channels are preferably positioned to match complementary protrusions 1004 in the optical component 1005 that is inserted in the mounting slot. Thus, when an optical component is inserted into a mounting slot, the protrusions located on the optical component will fit into the guide channels. The guide channels thereby assist in guiding the optical component into the mounting slot.

The depth to which the optical element is inserted into the mounting slot may be controlled by the length of the guide channel. For instance, as shown in FIG. 10A, the guide channel may extend some distance down the wall of a mounting slot to an end surface 1003. Once the leading surface 1006 of the complementary protrusion 1004 of the optical component reaches the end surface 1003 of the guide channel, the optical component will not be able to slide any further down into the guide channel. A mounting slot spring is preferably configured to press the cylindrical protrusions of the optical element into the guide channels, thereby achieving more accurate positioning of the optical element.

Very low assembly errors may be achieved through positioning features on each optical component and a silicon spring in each component mounting slot. Optical-element alignment to an accuracy of ±2 µm in position and ±0.5 mrad in rotation are achievable using the illustrated method. The accurate positioning of each optical element relative to other optical elements on the MOT may be guaranteed through the sub-micron-precision layout of the photomask from which the MOT is made.

Because diverse optical components can be embedded in the MOT, the optical components can be fabricated separately in substrates other than the MOT substrate and by means of processes other than the processes involved in MOT fabrication. For example, a refractive lens can be patterned in a photosensitive hybrid sol-gel material coated on a glass substrate, while the MOT may be fabricated in silicon. The refractive lens may fabricated using a grayscale photomask. The MOT, on the other hand, may be fabricated using a binary photomask. Finally, the disclosed MOT concept allows for replacement of individual optical elements without sacrificing the entire MOT.

4M Devices

One preferred embodiment of a multi-modal miniature microscope ("4M device") is shown in FIG. 1. The device of FIG. 1 uses lithographically fabricated refractive optical elements positioned vertically in silicon-spring mounting slots. The 4M devices may include a light source 11 mounted on the MOT 10. The embodiment shown in FIG. 1 also includes a collector mirror 12, a scanning grating 13, a folding flat mirror 14, a dichroic beam splitter 15, a plurality of lithographically patterned refractive lenses 16, a folding flat mirror 17, a photodetector 18, and an objective lens 19. The tissue 20 to be imaged is placed below the objective lens. Those skilled in the art will realize that the optical components of the microscope may be arranged in a variety of ways, that components may be added or taken away.

Light Source

The device includes a light source that may be designed to operate in any part of the spectrum from the ultraviolet to the near-infrared (NIR). Depending on the light source used, microscopes may be constructed to operate in the blue (for autofluorescence imaging), in the near-infrared (for reflectance imaging), or both in the blue and in the near infrared. The light source of the microscope may be integrated on the MOT as shown in FIG. 1. In another embodiment of the invention, such as is shown in FIG. 8A, a light source may not be mounted on the MOT. Instead, the light source may also be external to the MOT and connected via a variety of well known means, such as a fiber optic cable. Additionally, as new contrast agents continue to be developed, the present devices may operate at wavelengths chosen to match the excitation and emission spectra of the new contrast agents.

Autofluorescence spectroscopy, reflectance imaging, and confocal imaging (both of reflected light and autofluorescence) each provide information about tissue architecture and biochemical composition in near real-time without the need for tissue removal. Autofluorescence and confocal imaging provide tools to assess two fundamentally different sources of contrast between normal and neoplastic epithelium: differences in autofluorescence (which are related to metabolic rate, angiogenesis and collagen cross-linking) and differences in refractive index profiles (which are related to morphologic differences, primarily in the nucleus).

Autofluorescence provides a sensitive and specific tool to improve detection of neoplasia. Confocal imaging may be used to resolve sub-cellular detail throughout the entire epithelial thickness, providing sufficient contrast to enable quantitative feature analysis such as nuclear to cytoplasmic ratio. For example, confocal imaging may offer a clinically useful adjunct to standard histopathologic techniques for amelanotic tissue.

Depending upon the type of cancer that it desired to be imaged, different imaging wavelengths may be chosen. For instance, wavelengths of 380 nm and 460 nm correspond to diagnostically useful regions identified for detection of pre-cancers of both the cervix and the oral cavity. At 380-nm excitation, the co-factor NADH is the primary cellular fluorophore. At 460-nm excitation, FAD is the primary cellular fluorophore. Collagen crosslinks fluoresce at both excitation wavelengths.

It has previously been shown that using reflectance confocal imaging, images at tissue depths of 400 microns, penetrating the entire epithelium, can routinely be obtained. It is also believed that images throughout the epithelium may also be obtained using autofluorescence.

Additionally, the proposed illumination levels in the near UV do not pose significant safety concerns. For instance, at 380 nm illumination, exposure should not exceed 47 J/cm$^2$ for light sources and for lasers in this illumination region, exposure should not exceed 1 J/cm$^2$, with a limiting aperture of 3.5 mm diameter. It is estimated that the 4M devices will deliver between 500 µW and 1 mW of laser light to the tissue surface at 380 nm illumination and that total imaging time per field will be less than 1 minute.

It is anticipated that actual image-acquisition time will be much shorter, but this will enable the clinician or operator to examine the image and ensure that the optimal area is in the field of view. Averaging over the 3.5 mm limiting aperture, gives a total illumination level of (1 mW)(60 seconds)/(0.096 cm$^2$)=625 mJ/cm$^2$. The proposed illumination levels are 1.6 to 75 times less than the exposure levels allowed for lasers or light sources, respectively.

Scanning Grating

The MOT concept allows for the inclusion of components that provide functionality beyond that achievable with lenses alone. A specific example is optical sectioning of a three-dimensional (3D) specimen. Optical sectioning may be accomplished using structured illumination with a scanning amplitude grating that is projected into the 3D specimen. Images of the 3D specimen may be taken at three lateral positions of the scanning grating. The three images may next be processed in a simple manner to provide an optical-section image of the 3D specimen. The method is based on the simple principle that the amplitude grating appears in-focus only over a limited axial range. Outside that range, the amplitude grating may be out of focus and blurred. The out-of-focus blurring results in loss of modulation. Lateral motion of the amplitude grating therefore results in modulation of light that originates only within a thin section of a 3D specimen.

In one embodiment, the present invention uses a continually oscillating amplitude grating instead of a grating stepped to three discrete positions. The continuous motion of the amplitude grating will modulate in time the fluorescence signal from a thin section of the specimen. This approach may also include a custom CMOS active-pixel image sensor. Each active pixel may include a narrow temporal-frequency bandpass filter. Consequently, the proposed CMOS active-pixel image sensor only records signal that is modulated at or near a center frequency that corresponds to the scanning frequency of the amplitude grating.

A macroscopic amplitude grating will be translated perpendicular to the optical axis and a minimum of three images will be collected with a CCD camera to demonstrate functionality. The images may be subsequently combined to determine the autofluorescence distribution or reflectance variation at a fixed working distance.

Figure 7:
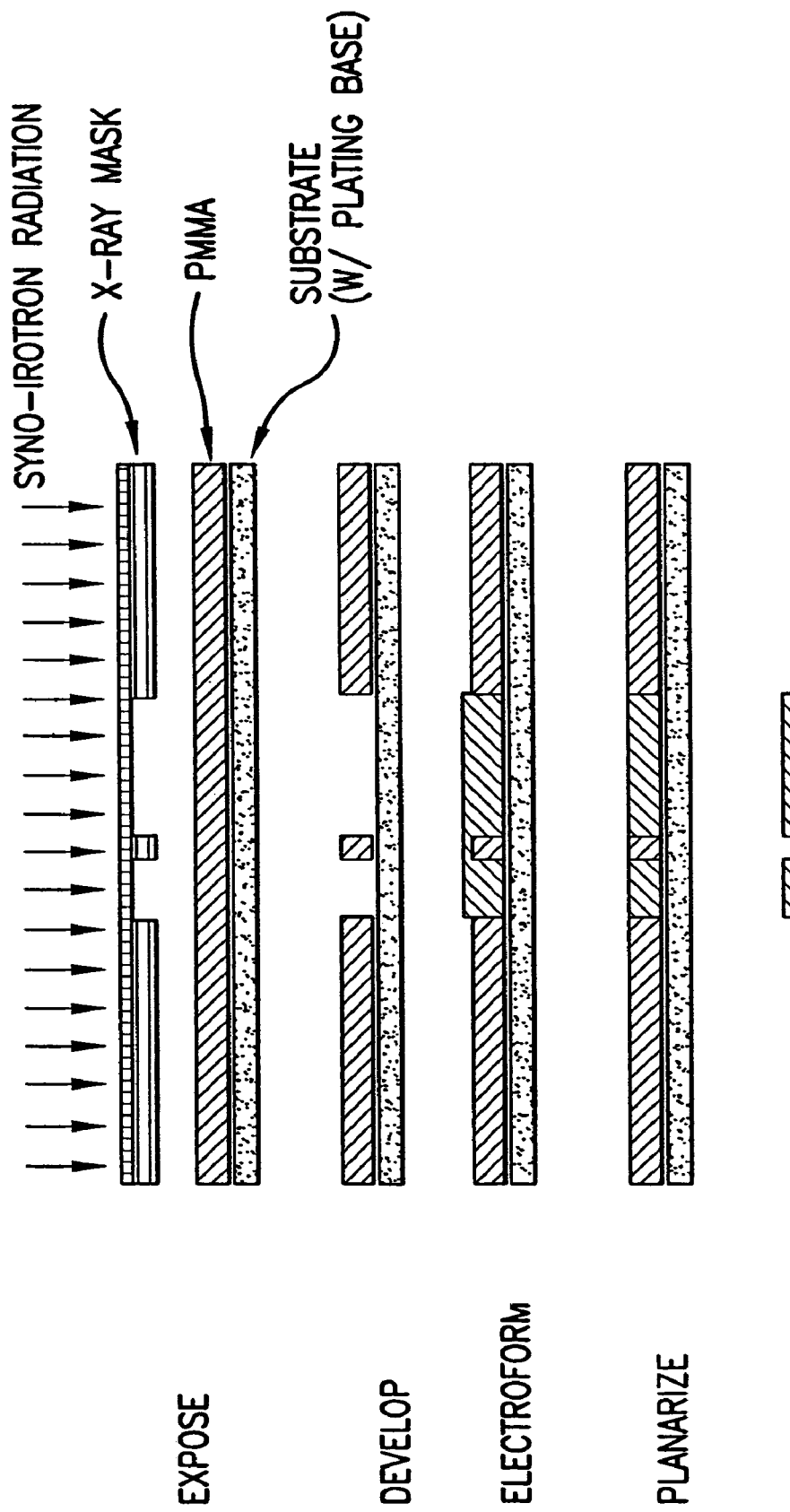
FIG. 7 shows the deep X-ray lithography DXRL process. The process steps shown are (1) exposure of a PMMA (poly-methymethacrylate) photoresist with x-rays generated from a synchrotron light source through an x-ray mask, (2) PMMA development to realize a plastic mold, (3) electro-deposition to fill this mold with a metal material, (4) planarization to accurately control part thickness, and (5) release and device integration.

Preferably, the prime mover for the miniature scanning grating is a variable reluctance magnetic microactuator constructed via deep x-ray lithography (DXRL) and electroforming processing. The basic DXRL and electroforming process flow is outlined in FIG. 7. With this process, arbitrarily shaped components with dimensions from 1 micron to several centimeters may be fabricated with sub-micron tolerances. The sidewall rms roughness of these components is below 20 nm. Materials that may be used in the process include an array of electroformed metals such as copper, nickel, nickel-iron, and gold as well as molded plastics and ceramic materials. Microactuator-drive designs may use a DXRL assembly plate that is mounted to the MOT substrate and accommodates all microactuator-drive components via press-fit joining. Press-fit joints have been demonstrated in a number of similar devices. DXRL processing enables extremely well controlled press-fit joints.

Design information from previously fabricated magnetic microactuators as outlined herein may be extrapolated and used to formulate designs appropriate for the 4M scanning grating drive. Extensive magnetic computer-aided design (CAD) tools exist and may be used to design a permanent-magnet-assisted linear magnetic microactuator with a resonant frequency of 100 Hz and motion range of ±100 µm. The microactuator resonant frequency may readily be increased to 400 Hz at the expense of increased power required to drive the microactuator. The microactuator resonant frequency may also be increased if 1/f noise in the image sensor requires such a change.

In one embodiment, a clamping scheme for sub-micron-precision positioning of the grating component that will be fabricated independent of the magnetic microactuator may be integrated. A flexure that supports a platform on which the grating is positioned may be fabricated with high yield strength electroplated material in order to provide good spring-like behavior. In the case of the 100-Hz microactuator, the anticipated power requirement, assuming a worst-case efficiency of 10%, is expected to be on the order of 100 microWatts (µW). The low drive impedance of a magnetic-microactuator drive will enable driving voltages of near 0.5 Volts with currents of a fraction of a milliAmpere (mA). The entire scanning-grating drive is expected to fit well within the MOT component design footprint, which in one embodiment may be approximately 2 mm×3 mm.

Figure 3:
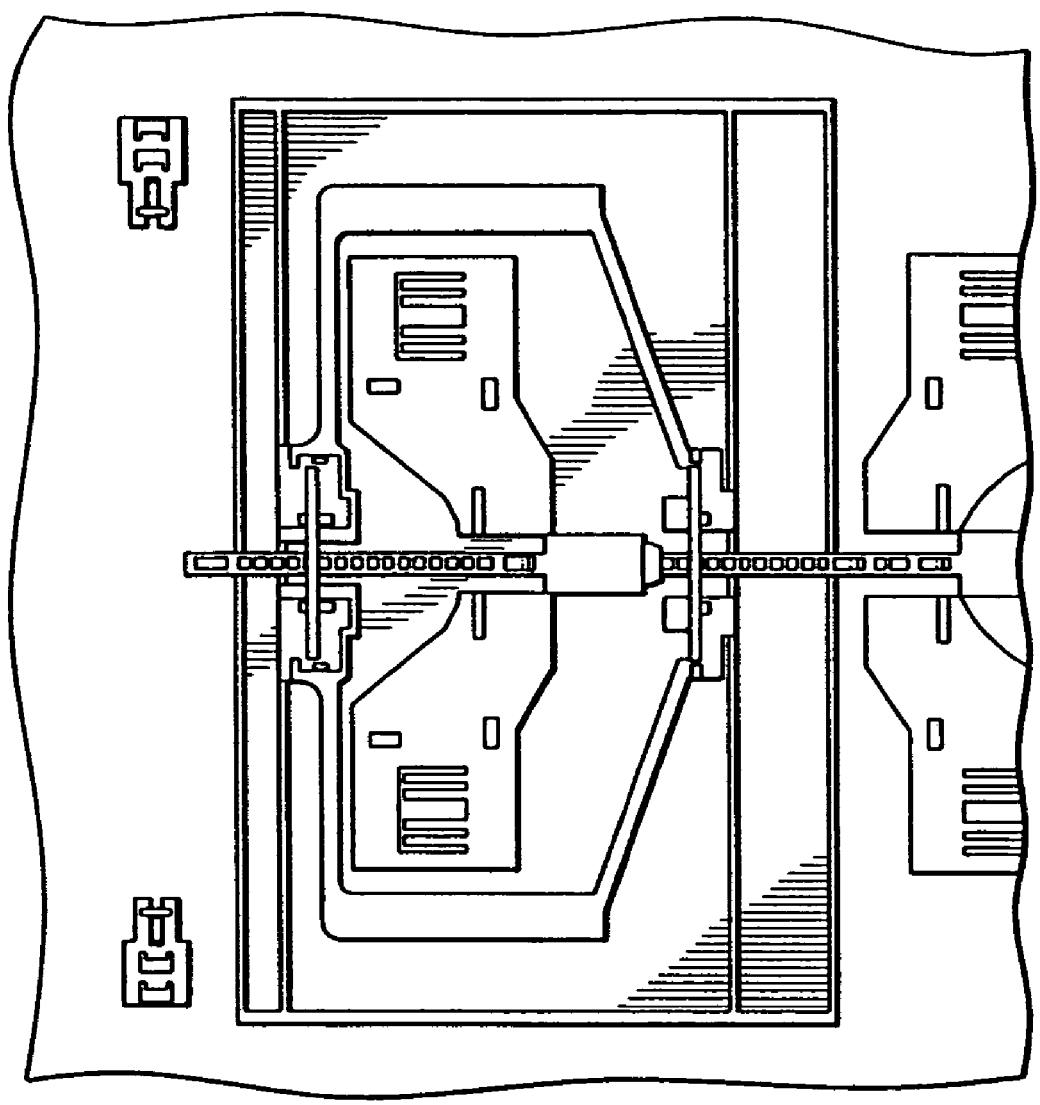
FIG. 3 shows a magnetic microactuator that may be adapted to the task of a scanning grating in one embodiment of the device of the present invention. Specifically, a partially assembled variable-reluctance magnetic linear microactuator is shown.

These microactuators have been used previously for positioning of variable wire-grid infrared filters and optical fiber switches, and are well suited for the task of scanning the grating in a 4M device. FIG. 3 shows a partially assembled example of this type of magnetic microactuator. In FIG. 3, a folded spring flexure is shown that supports a center driven plunger. The microactuator is capable of providing forces in the milli-Newton range with motion ranges of several hundred microns. Variable reluctance magnetic microactuators also can be operated in resonance in a closed-loop mode with high efficiency. Typical resonance frequencies are near 100 Hz and input powers of a few milliwatts are sufficient to drive the microactuator to the full extent of its motion.

One possible design of the scanning amplitude grating calls for a grating period of 15 microns. An amplitude grating of this period can be readily fabricated as chrome on glass using commercial microlithography processing. In the context of 4M devices, the trade-off involved in making the choice of grating period is between increasing the axial resolution and decreasing signal-to-noise ratio. Full-volume, optically-section imaging may be achieved by translation of the tissue relative to the 4M device. Additionally, the epithelium may be translated through the device focal plane using suction-based devices.

As will be understood by those having ordinary skill in the art with the benefit of the present disclosure, the scanning grating mechanism for translation of the grating may, in one embodiment, be fabricated as part of the substrate instead of having the scanning grating components being integrated into a separate substrate.

As previously stated, the 4M devices may achieve optical sectioning by structured illumination. One challenge associated with the structured-illumination method of optical sectioning is the expected high level of background signal when imaging turbid media. If the level of background signal precludes acquisition of image data with a useful signal-to-noise ratio, e.g., greater than 10, then instead of only projecting the scanning grating into a 3D medium, imaging may also be done through the grating. This approach is analogous to a Nipkow disk. Instead of a disk, however, a scanning grating is used. A dichroic filter (in case of autofluorescence imaging) may be placed behind the grating, unlike the configuration shown in FIG. 1. The background should be reduced by a factor of two in the case of a scanning grating with equally wide open and closed sections (i.e., "50% duty cycle"). An additional set of optics may be used to relay the image at the plane of the grating to the CMOS image sensor.

In one embodiment, a scanning grating system may be used in which illumination light passes through the grating twice. First, the illumination light passes when the grating is projected into the tissue, and second, illumination light passes when light is reflected or emitted from the tissue and propagating towards the image sensor. This "double-pass" grating system arrangement is similar in concept to a spinning Nipkow disc except that, in this embodiment, a grating may be translated. One advantage of this approach is that it achieves an increased suppression of background signal from the object as compared to a "single-pass" arrangement.

Patterned Refractive Lenses

As shown in FIG. 1, the 4M device may also comprise one or more lithographically patterned, refractive optical elements and a glass objective lens that may be mounted in the MOT silicon wafer. In one embodiment, the glass objective lens is spherical in shape and may be adapted from a commercially available ball lens. In one specific embodiment, the glass objective lens has a clear aperture of 800 microns and a thickness of 500 microns. The objective lens may be positioned in the MOT silicon wafer in a simple round aperture 81 etched through the silicon wafer 82, as shown in FIG. 8B. Alternatively, the lens may be positioned in the MOT silicon wafer by means of a multiple spring, circular self-centering mount that may be etched through the silicon wafer. All remaining components can be mounted in the MOT substrate as shown in FIG. 2.

Fabrication of Optical Elements

Figure 4A:
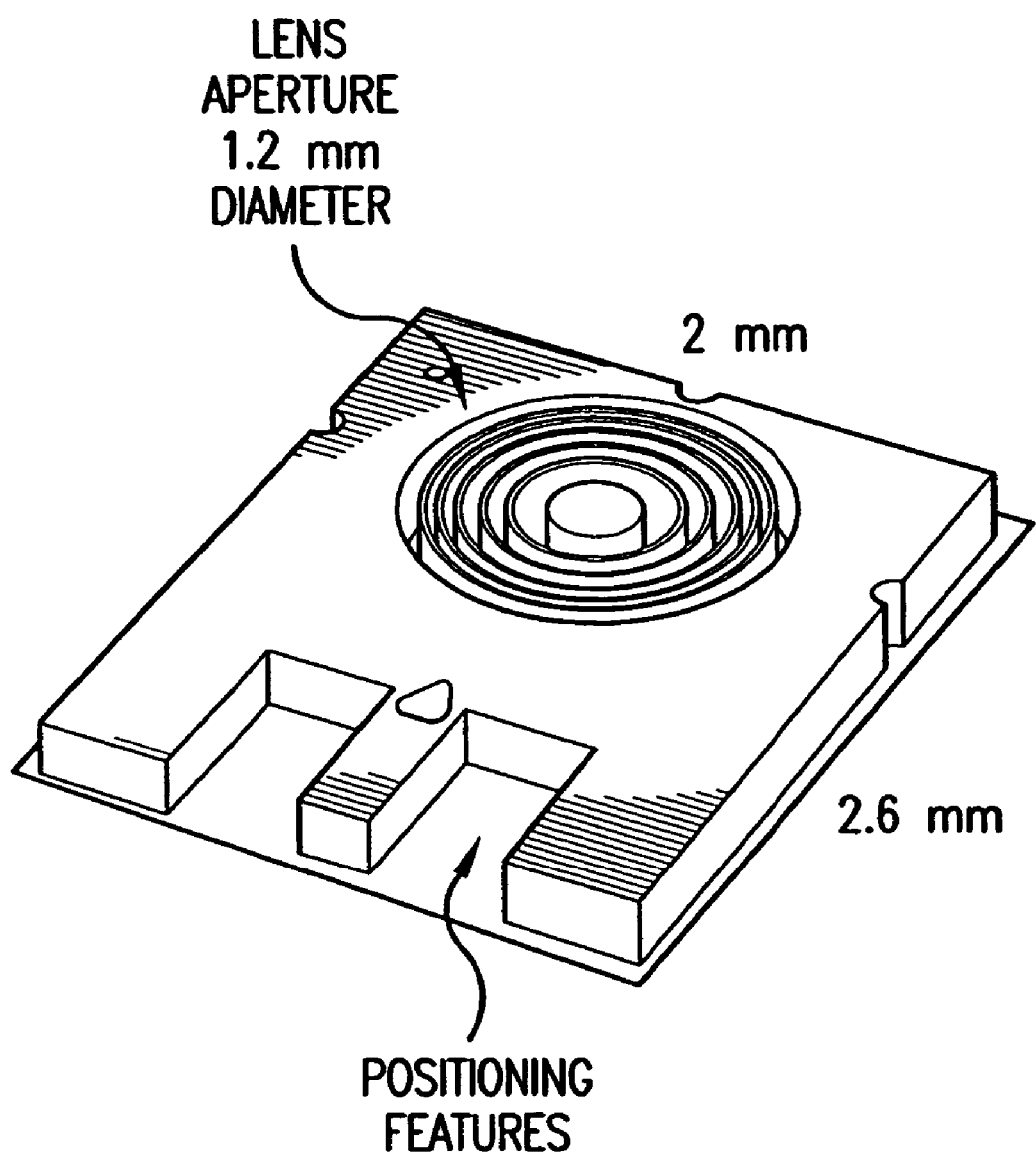
FIGS. 4A and 4B show lithographically patterned optical elements.
Figure 4B:
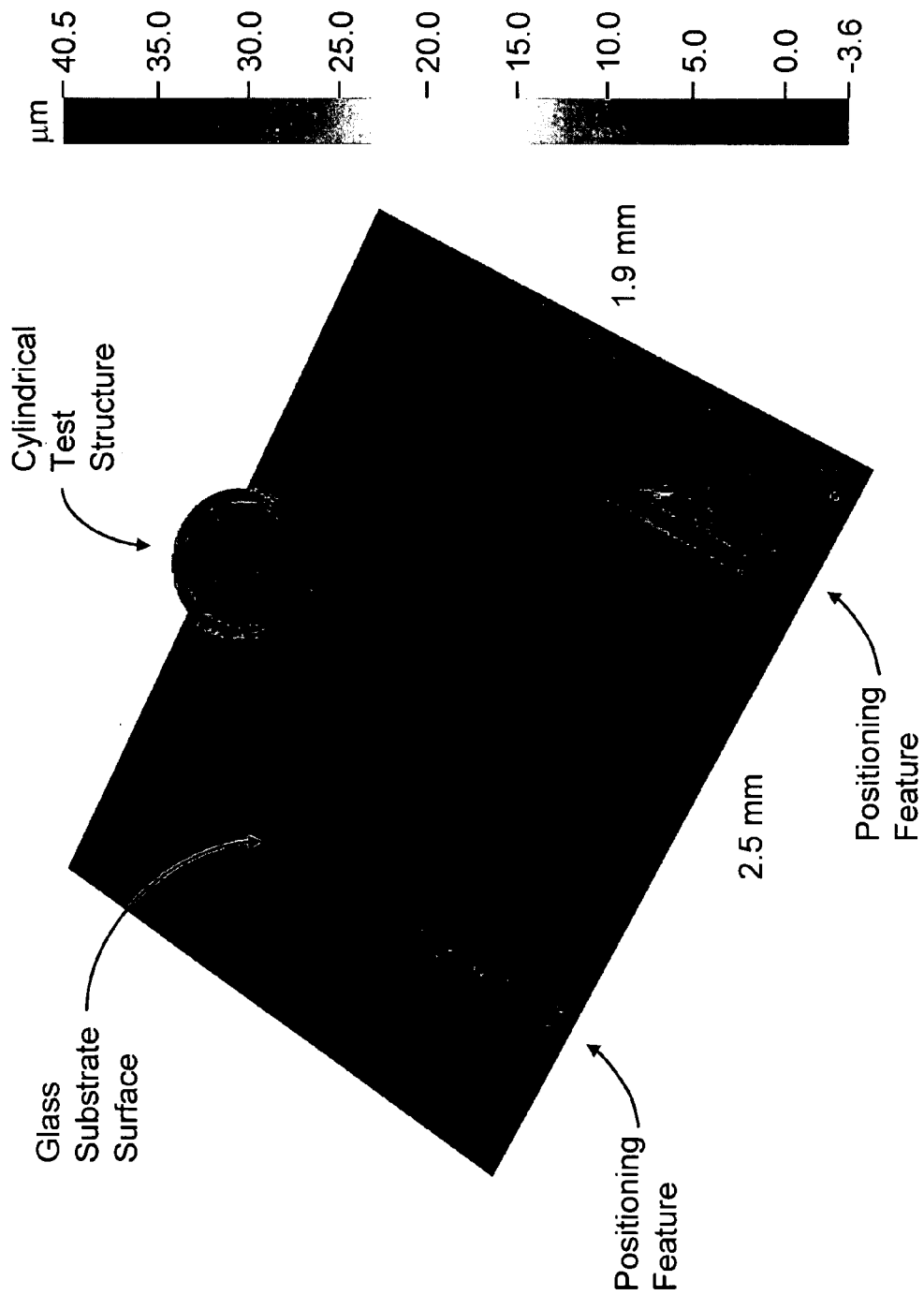
Figure 5A:
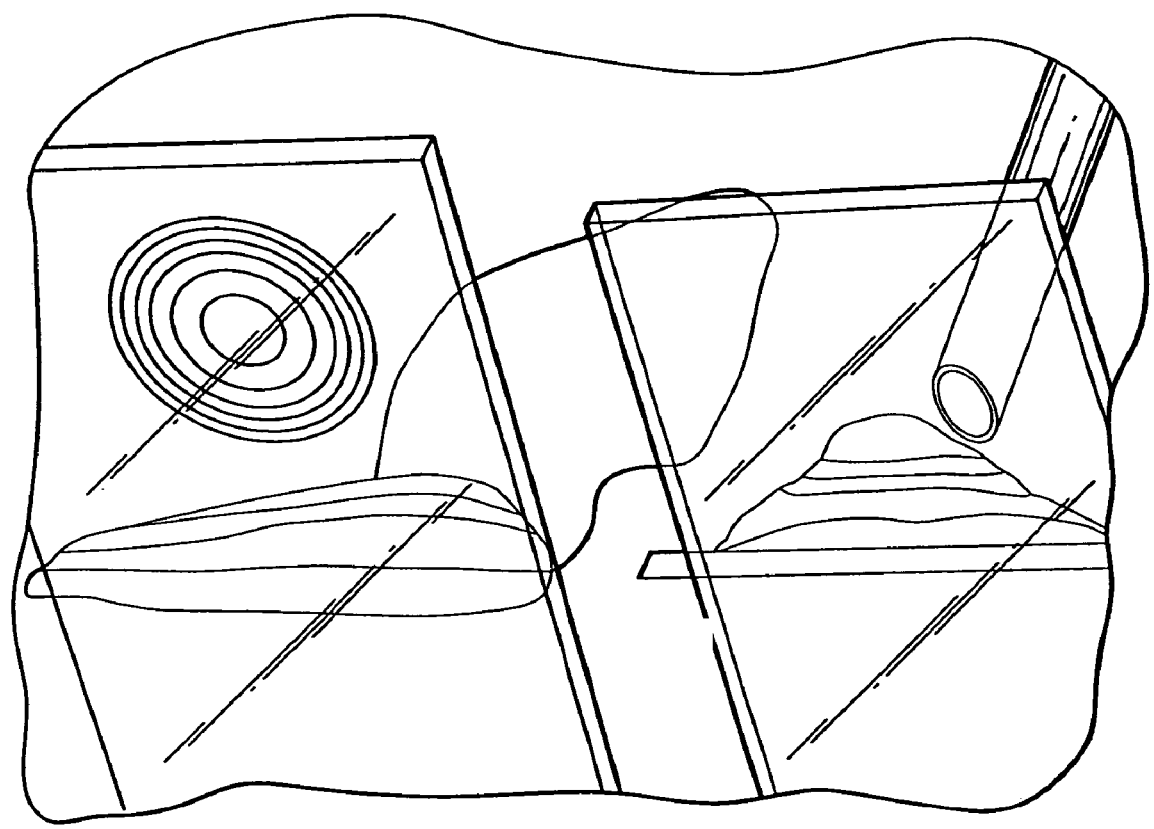
FIGS. 5A and 5B show lithographically patterned optical elements mounted and cemented in a silicon MOT substrate.
Figure 5B:
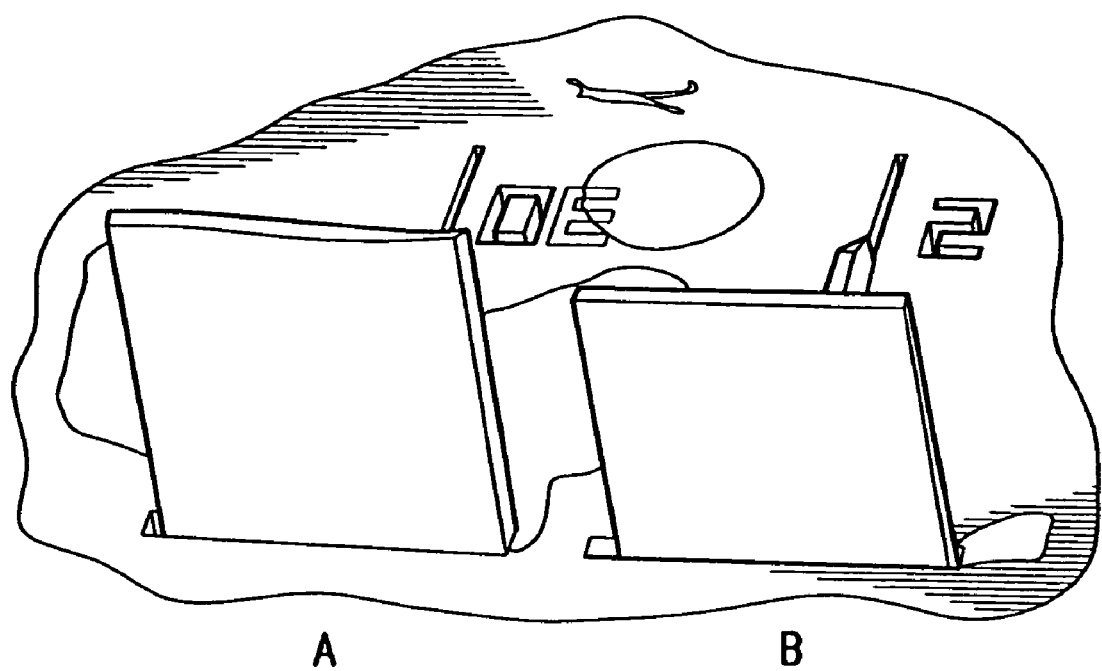

A preferred approach to fabrication of micro-optical and opto-mechanical structures is based on the sol-gel technique. The sol-gel technique has the unique potential for simultaneous fabrication of micro-optical and opto-mechanical structures by UV patterning in a single lithography step. No etching of patterned structures is required when using the sol-gel technique. Diffractive optical elements using binary and grayscale photomasks [see FIG. 4A and FIG. 5A] have previously been patterned. More recent patterning experiments demonstrate a doubled film thickness (34 μm) and an rms surface roughness of 20 nm, as shown in FIG. 4B. Reduced rms surface roughness means a reduction in undesired scattering from lithographically fabricated optical elements.

In one lithography step and using a grayscale photomask, a thick layer of hybrid sol-gel material may be patterned with a diffractive, a reflective, a refractive optical surface, or a combination thereof. In grayscale lithography, a standard spherical optical surface is as simple to fabricate as an arbitrary aspheric optical surface. To make a convex refractive lens, for instance, the hybrid sol-gel material may be spin-coated to form a 60-μm thick film on borosilicate glass substrates. After spinning, the films may be prebaked at 95° C. for 10 minutes to decrease the amount of solvents in the film. The baking step reduces the effect of photomask adhesion to the film and also improves the adhesion of the film to the glass substrate. Ultraviolet (UV) exposure may be accomplished by using a mercury UV lamp at a wavelength of 365 nm and a grayscale photomask.

The grayscale photomask may be designed to impart to the film an arbitrary surface. Lithographically fabricated optical elements may be characterized interferometrically to measure the accuracy of their surface figure and to determine their surface roughness. The accuracy of the surface figure determines the optical elements' first-order properties, e.g., the focal length, and the aberrations introduced by the optical elements. The surface roughness determines the fraction of light that is scattered by the optical elements, leading to reduced throughput and reduced contrast due to stray light. The scattering properties of the patterned hybrid sol-gel material may be further characterized in terms of a bi-directional scattering distribution function (BSDF). The BSDF determines the angular distribution of scattered light. The BSDF data may be used to increase the accuracy of modeling of 4M systems and to improve 4M designs by controlling stray light.

As previously indicated, in one embodiment the optical elements may be patterned to a depth of 60 microns. For a given lens-aperture size, the patterned depth establishes a lower limit on the focal length of a lithographically patterned optical element. Finally, it is preferable that the precursors used in hybrid sol-gel material processing be filtered to avoid the introduction of impurities that could give rise to autofluorescence of the fabricated optical elements.

CMOS Active-Pixel Arrays

One challenge associated with the structured-illumination method of optical sectioning is the expected high level of background signal when imaging turbid media. In the nominal structured-illumination approach, computational methods may be used to remove out-of-focus light. Consequently, system performance may ultimately be limited by the noise associated with fluorescence generated at out-of-focus planes.

One way to reduce the effect of the out-of-focus plane fluorescence background is to replace a standard CCD camera with a custom CMOS active-pixel image sensor with a narrow ($\Delta f=1$ Hz) tuned temporal-frequency band-pass filter at each pixel. The band-pass filter will block the unmodulated background fluorescence or reflected light that originates at planes below and above the optical section. This is based on the assumption that the noise spectral power density is constant as a function of temporal frequency, i.e., the noise is white. The band-pass filter will therefore also reduce the integrated noise power.

There are several additional methods by which the signal can be better discriminated from background. For instance, the DC background signal can be reduced by a factor of two by illuminating and imaging through a scanning grating. Additionally, the oscillation frequency of the micro-mechanical scanning grating, i.e., the carrier frequency, may be increased. From a theoretical viewpoint, the increase in the oscillation frequency (i.e. from 30 Hz to 100 Hz) should result in at least a three-fold decrease in noise power. Furthermore, every pixel in the image sensor may also contain a 1-Hz band-pass filter to further limit the integrated noise power.

CMOS active-pixel image sensors have become serious competitors to CCDs (and any other image sensing technique) in virtually all imaging applications. CMOS is especially appropriate in the present application due to the system advantage of signal processing in each pixel such as bandpass filtering. In one preferred embodiment, the filter's bandpass is centered at 100 Hz, which is the modulation frequency of the reflectance or autofluorescence signal resulting from the motion of the scanning grating. The images recorded with this kind of custom active-pixel image sensor will correspond directly to the reflectance variation or autofluorescence distribution at the object depth and no post-processing of multiple images will be necessary.

Readily available, sub-micron CMOS fabrication processes will support implementation of the photo-diode and signal processing circuits within a pixel area of 15 μm×15 μm or less. A 100×100 pixel array with peripheral support circuits should easily fit on a chip of 2 mm×2.5 mm or less. These chip dimensions are compatible with the requirements of the embodiment of the 4M device shown in FIG. 1.

In one embodiment of the present invention, the image recorded on the CMOS active-pixel image sensor may be magnified electronically rather than optically for viewing by eye, i.e., the image will be displayed scaled up. Such electronic magnification is equivalent to the optical function performed by an eyepiece: In each case, the user perceives the final image at a comfortable viewing distance, e.g., 250 mm.

Additionally, the field of view of the 4M devices may be expanded in many ways. This is desirable because it allows for more efficient imaging. The field of view may be expanded, for example, by introducing additional, low-magnification imaging systems on one MOT substrate alongside the miniature microscope. This may be accomplished without significantly increasing the size of the microscope. Alternatively, "contact" imaging may be possible whereby the bottom surface of the microscope device is itself a low-resolution image sensor.

Even with a limited field of view, an imaging device capable of sub-cellular resolution has important clinical roles. First, clinicians already use their visual recognition skills to decide where to obtain diagnostic biopsies. Using the present microscope devices to interrogate these areas may reduce the costs of detecting pre-cancer by better guiding biopsy during such procedures as colposcopy or visual examination of the oral cavity. Second, the microscopes may be similarly used at the time of tumor resection to aid in margin detection. Third, 4M devices may be used to facilitate chemoprevention studies in the cervix and the oral cavity.

Studies

Reflectance Imaging Preliminary Studies

The preliminary imaging studies presented here emphasize imaging of tissue sections that are perpendicular to the planes that will be imaged with the 4M devices. However, these preliminary data may be useful in interpreting the image data to be acquired eventually by 4M devices.

The use of high-resolution, in vivo confocal imaging may offer a clinically useful adjunct to standard methods for the diagnosis and screening of epithelial pre-cancers. A reflectance-based confocal microscope was used to image cervical cells and colposcopically normal and abnormal cervical biopsies. Images were obtained before and after the application of 6% acetic acid. The confocal microscope resolved sub-cellular details throughout the entire epithelial thickness. Normal and abnormal cervical tissue were clearly differentiable. Addition of acetic acid enhanced nuclear signal in all acquired images. Confocal images of a short-term tissue culture of cervical tissue show the increase in nuclear-to-cytoplasmic ratio throughout the epithelium (see FIG. 15). These preliminary studies show that high-contrast, reflected-light images of cervical tissue are attainable in near real-time using a conventional confocal microscope.

Autofluorescence Imaging Studies

While a number of clinical studies have demonstrated that fluorescence spectroscopy can provide highly sensitive, specific, and cost-effective diagnosis of cervical precancers, the underlying biochemical mechanisms responsible for differences in fluorescence spectra of normal and dysplastic tissue are not fully understood. It has recently been demonstrated that short-term tissue cultures of normal and neoplastic tissue could be used to assess differences in autofluorescence of normal and dysplastic tissue and to understand the biological basis for these differences. Short-term tissue cultures represent a novel, biologically appropriate model for understanding epithelial autofluorescence.

Transverse, short-term tissue cultures were prepared from colposcopically normal biopsies in a 31-patient study and from normal and abnormal biopsies in a 34-patient study. Autofluorescence images were acquired at 380 and 460 nm excitation. At both excitation wavelengths, measurable epithelial and stromal autofluorescence was detected. The autofluorescence of both tissue layers was found to be age and hormone-status dependent. Fluorescence images were placed into groups: (Group 1) bright epithelial and weak stromal fluorescence, (Group 2) similar epithelial and stromal fluorescence, and (Group 3) weak epithelial and bright stromal fluorescence. The average ages of women in the groups were 30.9, 38.0, and 49.2 years. Epithelial fluorescence intensity was similar in Groups 1 and 2, but weaker in Group 3. Stromal intensity was similar in Groups 2 and 3, but weaker in Group 1. The ratio of epithelial to stromal fluorescence intensity was significantly different for all groups. These results suggest a biological basis for the increased fluorescence seen in older, postmenopausal women.

With the development of dysplasia, statistically significant increases in epithelial fluorescence intensity were observed at 380 nm excitation in pre-cancerous tissue [106±39 in arbitrary units (AU)] relative to normal tissue (85±30 AU). The fluorophore responsible for this increase is likely NADH. Stromal fluorescence intensities in the dysplastic samples decreased at both 380 nm [102±34 (pre-cancer) vs. 151±44 (normal)] and 460 nm excitation [93±35 (pre-cancer) vs. 137±49 (normal)], i.e., wavelengths at which collagen is excited. A tissue's metabolic state is sometimes described by calculating the "redox ratio," a quantity obtained by dividing the fluorescence of FAD by the summed fluorescence of FAD and NADH. The redox ratio which typically decreases in cancer, is sensitive to changes in metabolic rate and vascular oxygen supply. In principle, the Blue 4M device may be adapted to simultaneously record both fluorescence signals, to measure the redox ratio directly.

Decreased redox ratio (17% to 40% reduction), indicative of increased metabolic activity, was observed in the pre-cancerous samples. These results provide valuable insight into the biological basis of differences in fluorescence of normal and pre-cancerous cervical tissue. Furthermore, the results show that short-term tissue cultures provide a novel biological system to explore the optical changes that accompany the development of pre-cancer in human tissue. This model system can be used to further explore the capabilities of 4M devices in both autofluorescence and reflectance mode, assessing the devices' ability to discriminate the changes in morphology and biochemistry that accompany the development of pre-cancer in human tissue.

Testing

Potential configurations of 4M device can be tested using ANSYS to predict the mechanical and thermal properties of the planned 4M devices. Thermal analysis using ANSYS will predict the effects of power-dissipation due to the light source, the scanning grating, and the CMOS image sensor. This analysis may be used to control the cumulative effect of power dissipation on the imaging function of a fully integrated 4M device. In addition, detailed simulations of the 4M-device optics can be performed using ASAP, a non-sequential ray tracing (NSRT) program. NSRT analysis may be used to quantitatively determine the contrast-reducing effects of light scattering from the lithographically fabricated optical elements and any other sources of stray light within the 4M device. Most significantly, NSRT analysis can be used to suppress any these effects, by means of micro-baffles, for instance.

4M devices may be tested, for example, in three biologically appropriate models of normal and neoplastic oral-cavity epithelium. Tissue-engineering methods may be used to develop three dimensional organotypic cultures of normal and neoplastic oral cavity and cervix. Secondly, short-term tissue cultures of normal and neoplastic oral cavity and cervical tissue from tissue biopsies can be prepared. Third, an animal model of oral-cavity neoplasia, the hamster cheek pouch model of carcinogenesis, may be used. These model systems will provide data from biologically relevant specimens of normal and neoplastic epithelium that will allow for the testing of 4M devices.

Organotypic Cultures

Growing cells as an adherent monolayer in plastic dishes or in suspension culture is technically simple. Therefore, it is the major method that cell biologists use to study animal and human normal and original phenotypic characteristics. Cells are separated from different types (e.g., mesenchymal cells are separated from epithelial cells) to prevent one type from dominating another when their growth rates or growth requirements vary. The maintenance of the various tissue components in their normal anatomical relationship is important for regulation of growth and differentiation. Tumor cells, stromal fibroblasts, or endothelial cells, may express a set of genes in situ that only partially overlaps the set of genes expressed by each cell type in isolation from the others in primary cultures.

In addition, the mesenchymal cells may secrete factors that the tumor cells can use as mitogens. Organotypic cultures have been developed initially for skin and then adapted for a variety of epithelial cancers as an approach to provide three dimensional growth with epithelial cell-epithelial cell interactions that are major features of solid carcinomas and are lost partially in monolayer cultures. The method is based on the growth of epithelial cells at the air-liquid interface on top of a reconstituted collagen gel containing fibroblasts.

This organ culture provides conditions that preserve tissue architecture, growth, and function. It can be prepared with different cell layers and can be analyzed as a tissue without restrictions involved in obtaining actual surgical specimens from patients or volunteers. Organ cultures are also more reproducible than tissues obtained from different individuals. It is believed that pre-clinical research would benefit from analysis of novel diagnostic approaches directly in organotypic cultures. The results are likely to be more informative and can be extrapolated to the in vivo situation with greater confidence than work with cell lines in monolayer cultures. Therefore, short-term organotypic cultures of oral cancer cells may be used to determine the efficacy of new diagnostic approaches such as those proposed here.

Organotypic cultures of normal cervix, cervical neoplasia, and oral-cavity neoplasia may be examined using 4M devices designed to measure autofluorescence. Using 380 and 460 nm excitation, analysis can be done as to how well the 4M device separates fluorescence of the epithelial cells from the supporting stroma and how effectively signals from normal and neoplastic samples can be separated. Similar tests can also be performed to record reflected-light optical-section images. The performance of 4M devices can be characterized based on autofluorescence and reflectance in terms of signal-to-noise ratio, penetration depth, and the ability to separate normal and neoplastic samples.

Short-term Tissue Cultures

While organotypic cultures allow for the examination of autofluorescence and reflectance in a three-dimensional geometry, there may be differences in the fluorescence of the cell lines used in this model system and the pre-cancerous epithelial cells found in lesions in vivo. The second testing model overcomes this limitation. Short-term cultures of normal and neoplastic biopsies obtained from patients can be prepared. For instance, biopsies (2 mm×4 mm×1 mm) of the oral cavity and the cervix may be obtained from patients. Preferably, cervical biopsies will be obtained from women being seen for colposcopy because of an abnormal Pap smear. Preferably, biopsies of the oral cavity will be obtained from patients suspected to have an oral-cavity cancer. Biopsies should be obtained from a normal-appearing area and an area suspected for dysplasia. The biopsies may placed in chilled culture medium (DMEM without phenol red), and embedded in 4% agarose for slicing. A Krumdieck Tissue Slicer (Alabama Research and Development MD1000-A1) may then be used to obtain 200 µm thick fresh tissue slices, cut perpendicular to the epithelial surface. Fluorescence and reflectance images can then be obtained from tissue slices within 1.5 to 5 hours of biopsy. Control experiments show that fluorescence intensities are stable to within ±10% for up to 5.5 hours after preparation of the slices.

Animal Models

Organotypic cultures and short-term tissue cultures do not allow for the monitoring of lesion progression over time or to examine the effects of angiogenesis. Thus, an animal model may be used for further testing of 4M devices. The hamster cheek pouch carcinogenesis model, using chronic treatments of dimethylbenz[α]anthracene (DMBA) may be used as a model system to investigate changes in epithelial tissue fluorescence throughout the dysplasia-carcinoma sequence. Images may be taken weekly using both autofluorescence at 380 and 460 nm excitation and reflected light at 800 nm from both DMBA treated animals and control animals. Histopathology may be obtained at regular intervals throughout the study.

Previous studies that have investigated the autofluorescence of this model at weekly intervals and found that diagnostic algorithms based on autofluorescence can separate neoplastic and non-neoplastic tissue with 95% sensitivity and 93% specificity. The greatest contributions to diagnostic algorithms were obtained with excitation in the 370-380 nm wavelength range. This result was similar to that found in an in vivo study of both cervical and human oral-cavity neoplasia. Consequently, the hamster-cheek-pouch model is very well suited to characterize the performance of the 4M devices. Changes in fluorescence intensity are apparent as early as three weeks following initial treatment with DMBA, while morphologic changes associated with dysplasia occur on average at 7.5-12.5 weeks following initial treatment. Performance of 4M devices in imaging autofluorescence and reflected light in these models may be compared in terms of SNR, penetration depth, and the ability to separate normal and neoplastic samples (quantified in terms of sensitivity and specificity as compared to histopathology).

Contrast Agents

The techniques of this disclosure may be used in conjunction with any type of contrast agent. For instance, any type of dye may be used, including a dye conjugated to any type of antibody. For instance, a dye may be conjugated to an antibody for cytokeratins. Such a dye may be, for instance, Nile Blue A and/or Texas Red. Further, in different embodiments, one may use reflective nanoparticles to aid in imaging. For example, in one embodiment, gold nanoparticles may be used to increase imaging contrast. In another embodiment, quantum dots may be used.

EXAMPLES

NA=0.4 Red 4M Device

The proposed 4M device shown in FIG. 1 is water-immersion, has a numerical aperture of NA=0.4, a working distance of WD=250 μm, a field of view 300 μm in diameter, a transverse magnification of m=−4, and is designed for monochromatic operation at 800 nm. Due to the wavelength choice, this is called the "Red" 4M device. The value of the NA is bounded by a 60-μm maximum thickness of the UV-patternable hybrid sol-gel material that we expect to reach in Year One. The Red 4M device shown in FIG. 1 is designed for use with an array of photodetectors that are spaced by 10 μm.

The lateral resolution of this Red 4M device at the tissue level is expected to be approximately 5 microns. Those skilled in the art will realize that other 4M devices may be based on a configuration similar to that shown in FIG. 1. The primary difference will be an increased NA and a lateral resolution at the tissue level of approximately 3 microns. Additionally, other light sources may be used that operate over a variety of wavelengths. Additionally, a plurality of light sources could be used, and each light source could operate in various wavelength ranges.

The 4M device shown in FIG. 1 has been analyzed in terms of fabrication and assembly tolerances. Table 1 lists the top four tightest design tolerances. These tolerances have to be met for the optics of the 4M device in FIG. 1 to remain diffraction-limited in imaging performance. The expected lens-positioning accuracy of ±2 μm and rotation accuracy of ±0.5 mrad compare very favorably with the position and rotation tolerances required by the 4M device. The radius-of-curvature tolerance is a "precision" tolerance and will be achieved by fabricating multiple replicas of each lens and then selecting those lenses that are within the specified tolerance. The index-of-refraction tolerance is a loose, "commercial" tolerance.

TABLE 1

Selected four tightest fabrication and assembly tolerances associated with NA = 0.4 Red 4M device.

| Tolerance Type | Tolerance Values |
| --- | --- |
| Radius of curvature | ±0.3% |
| Hybrid sol-gel material index of refraction | ±0.001 |
| Position of lithographically patterned lenses | ±10 μm (lat); ±10 μm (vert.); −0/+3 μm (axial) |
| Rotation of lithographically patterned lenses | ±8 mrad |

NA=0.6 Red 4M Device

The proposed 4M device shown in FIG. 9 is a water-immersion Red 4M device designed to operate with a numerical aperture of NA=0.6, a working distance of WD=250 μm, a field of view 250 μm in diameter, a transverse magnification of m=−4. This 4M device is designed for monochromatic operation at 800 nm. FIG. 9 shows a schematic diagram of this preliminary design. A significant feature of the NA=0.6 design is that the relative positions of the optical elements remain the same as in previously introduced 4M devices. Consequently, the MOT silicon substrate shown in FIG. 8B needs no modification and can be re-used for this higher-performance miniature microscope. The relatively low-cost optical elements, on the other hand, can be readily modified according to the design's specifications.

NA=0.4 Blue 4M Device

The Blue 4M device needs to be designed for imaging over a wavelength range extending from 380 nm to 500 nm. A design similar in form and specifications to that shown in FIG. 9 has been developed. There are two major differences between the Red and Blue 4M-device designs: (1) the ball lens from which the objective lens may be fashioned in the Blue 4M device may be made from a lower-dispersion glass than its counterpart in the Red 4M device design, and (2) the lens labeled "1" in FIG. 9 is a combination diffractive-refractive lens. The use of a properly selected diffractive surface all but compensates for any longitudinal (a.k.a. axial) and lateral chromatic aberrations that may be encountered in the design.

REFERENCES

Each of the references listed below are hereby incorporated by reference.

S. Silverman, M. Gorsky, and F. Lozada, "Oral leukoplakia and malignant transformation. A follow up study of 257 patients," *Cancer*, 53, pp. 563-68 (1984).

The 1988 Bethesda System for reporting cervical/vaginal cytologic diagnoses. National Cancer Institute Workshop. JAMA 1989; 262:931-934.

L. G. Koss, "The Papanicolaou test for cervical cancer detection. A triumph and a tragedy" [see comment citation in Medline]. JAMA 1989; 261:737-743.

S. Lam, T. Kennedy, M. Unger, Y. E. Miller, D. Gelmont, V. Rush, B. Gipe, D. Howard, J. C. LeRiche, A. Coldman, and A. F. Gazdar, "Localization of Bronchial Intraepithelial Neoplastic Lesions by Fluorescence Bronchoscopy," Chest 113 (2), 696-702 (1998).

S. Lam, C. MacAulay, J. Hung, J. LeRiche, A. E. Profio, and B. Palcic, "Detection of Dysplasia and Carcinoma In Situ with a Lung Imaging Fluorescence Endoscope Device," J of Thoracic & Cardiovascular Surgery 105 (6), 1035-40 (1993).

B. W. Pogue, G. C. Burke, J. Weaver, D. M. Harper, "Development of a Spectrally Resolved Colposcope for early detection of Cervical Cancer," in Biomedical Optical Spectroscopy and Diagnostics Technical Digest (Optical Society of America, Washington D.C., 1998), 87-89.

S. L. Jacques, J. R. Roman, and K. Lee, "Imaging Superficial Tissues with Polarized Light," Lasers Surg. Med. 26, 119-129 (2000).

C. Smithpeter, A. Dunn, R. Drezek, T. Collier, R. Richards-Kortum, "Real Time Confocal Microscopy of In Situ Amelanotic Cells: Sources of Signal, Contrast Agents and Limits of Contrast," *Journal of Biomedical Optics,* 3:429-36, 1998.

L. T. Perelman, V. Backman, M. Wallace, G. Zonios, R. Manoharan, A. Nusrat, S. Shields, M. Seiler, C. Lima, T. Hamano, I. Itzkan, J. Van Dam, J. M. Crawford, and M. S. Feld, "Observation of Periodic Fine Structure in Reflectance from Biological Tissue: A New Technique for Measuring Nuclear Size Distribution," Physical Review Letters, vol. 80, pp. 627-630, 1998.

J. R. Mourant, I. J. Bigio, J. Boyer, R. L. Conn, T. Johnson, and T. Shimada, "Spectroscopic Diagnosis of Bladder Cancer with Elastic Light Scattering," Lasers in Surgery and Medicine, vol. 17, pp. 350-357, 1995.

I. J. Bigio, J. R. Mourant, J. D. Boyer, T. M. Johnson, T. Shimada, and R. L. Conn, "Noninvasive Identification of Bladder Cancer with Subsurface Backscattered Light," presented at Advances in Laser and Light Spectroscopy to Diagnose Cancer and Other Diseases, Los Angeles, Calif., 1994.

I. J. Bigio, J. D. Boyer, T. M. Johnson, J. Lacey, and J. R. Mourant, "Detection of Gastrointestinal Cancer by Elastic Scattering and Absorption Spectroscopies with the Los Alamos Optical Biopsy System," presented at Advances in Laser and Light Spectroscopy to Diagnose Cancer and Other Diseases II, San Jose, Calif., 1995.

Sokolov K., Drezek R., Gossage K., and Richards-Kortum R. Reflectance Spectroscopy with Polarized Light: Is it Sensitive to Cellular and Nuclear Morphology.—Optics Express, 1999, v. 5, No. 13, pp. 302-317.

R. R. Alfano, G. C. Tang, A. Pradham, W. Lam, D. S. J. Choy, and E. Opher, "Fluorescence Spectra from Cancerous and Normal Human Breast and Lung Tissues," IEEE Journ. Quant. Electron., vol. QE-23, pp. 1806-1811, 1987.

R. M. Cothren, R. Richards-Kortum, M. V. Sivak, M. Fitzmaurice, R. P. Rava, G. A. Boyce, M. Doxtader, R. Blackman, T. B. Ivanc, G. B. Hayes, M. S. Feld, and R. E. Petras, "Gastrointestinal tissue diagnosis by laser-induced fluorescence spectroscopy at endoscopy," Gastrointest. Endosc., vol. 36, pp. 105-111, 1990.

R. M. Cothren, R. Richards-Kortum, M. V. Sivak, M. Fitzmaurice, R. P. Rava, G. A. Boyce, M. Doxtader, R. Blackman, T. B. Ivanc, G. B. Hayes, M. S. Feld, and R. E. Petras, "Gastrointestinal tissue diagnosis by laser-induced fluorescence spectroscopy at endoscopy," Gastrointest. Endosc., vol. 36, pp. 105-111, 1990.

S. Lam, C. MacAulay, J. Hung, J. LeRiche, A. E. Profio, and B. Palcic, "Detection of dysplasia and carcinoma in situ with a lung imaging fluorescence endoscope device," J. Thorac. Cardiovasc. Surg., vol. 105, pp. 1035-1040, 1993.

K. Svanberg, S. Andersson-Engels, R. Berg, J. Johansson, S. Svanberg, and I. Wang, "Tissue Characterization in Different Malignant Tumors Utilizing Laser-Induced Fluorescence," presented at Advances in Laser and Light Spectroscopy to Diagnose Cancer and Other Diseases II, San Jose, Calif., 1995.

T. Vo-Dinh, M. Panjehpour, B. F. Overholt, C. Farris, F. P. Buckley, and R. Sneed, "In Vivo Cancer Diagnosis of the Esophagus Using Differential Normalized Fluorescence (DNF) Indices," Las. Surg. Med., vol. 16, pp. 41-47, 1995.

M. Follen Mitchell, S. B. Cantor, N. Ramanujam, G. Tortolero-Luna, R. Richards-Kortum, "Fluorescence Spectroscopy for Diagnosis Squamous Intra-Epithelial Lesions of the Cervix," Obstetrics and Gynecology, 93:462-70, 1999.

N. Ramanujam, M. Follen Mitchell, A. Mahadevan-Jansen, S. L. Thomsen, G. Staerkel, A. Malpica, T. Wright, N. Atkinson, R. Richards-Kortum, "Cervical Pre-Cancer Detection Using a Multivariate Statistical Algorithm Based on Laser Induced Fluorescence Spectra at Multiple Excitation Wavelengths," Photochemistry and Photobiology, 6:720-35, 1996.

M. Follen Mitchell, S. B. Cantor, C. Brookner, U. Utzinger, G. Staerkel, R. Richards-Kortum, "Receiver Operator Characteristic Curve of Fluorescence for the Screening of SILs," 94:889-896, Obstetrics and Gynecology, 1999.

D. Heintzelman, U. Utzinger, H. Fuchs, A. Gillenwater, R. Jacob, B. Kemp, R. Richards-Kortum, "Optimal Excitation Wavelengths for In Vivo Detection of Oral Neoplasia Using Fluorescence Spectroscopy," *Photochemistry and Photobiology,* 72(1): 103-113, 2000.

T. Collier, P. Shen, B. de Pradier, K. Sung, A. Malpica, M. Follen, R. Richards-Kortum, "Near real time confocal microscopy of amelanotic tissue: Dynamics of aceto-whitening enable nuclear segmentation," *Optics Express,* 6, pp. 40-48 (2000).

G. J. Kelloff, C. W. Boone, J. A. Crowell, V. E. Steele, R. Lubet, L. A. Doody, "Surrogate endpoint biomarkers for phase II cancer chemoprevention trials," J Cell Biochem Suppl;19:1-9 (1994).

M. B. Daly, "The chemoprevention of cancer: Directions for the future," Cancer Epidemiol Biomarkers Prev;2:509-12 (1993).

D. S. Goodman, "Basic Optical Instruments," Ch. 4 in *Geometrical and Instrumental Optics,* D. Malacara, ed. (Academic Press, 1988).

Survey of microscope-objective patents from 1976 to 1990, M. R. Descour, unpublished.

R. H. Webb and C. K. Dorey, "The pixilated image" in *Handbook of Biological Confocal Microscopy,* J. B. Pawley, ed., Ch. 4 (1995).

R. Levy, M. R. Descour, R. J. Shul, C. L. Willison, M. E. Warren, T. Kololuoma and J. T. Rantala, "A concept for zero-alignment micro optical systems," *Proc. of Micromachine Technology for Diffractive and Holographic Optics,* S. H. Lee and J. A. Cox, eds., SPE 3879-18 (September 1999).

M. A. A. Neil, R. Juškaitis, and T. Wilson, "Method of obtaining optical sectioning by using structured light in a conventional microscope," *Opt. Lett.,* 22, No. 24, 1905 (Dec. 15, 1997).

M. Kufner and S. Kufner, *Micro-Optics and Lithography,* Ch. 9 (VUB Press, 1997)

H. Guckel, T. R. Christenson, T. Earles, K. J. Skrobis, J. Klein, "Laterally Driven Electromagnetic Actuators," 1994 Solid-State Sensor and Actuator Workshop, Hilton Head Island, N.C., pp 49-52

T. R. Ohnstein, J. D. Zook, H. B. French, H. Guckel, T. Earles, J. Klein, P. Mangat, "Tunable IR Filters with Integral Electromagnetic Actuators," Tech. Digest of the 1996 Solid-State Sensor and Actuator Workshop, Hilton Head Isl., S.C., pp. 196-199 (1996).

[1]H. Guckel, HARMST Conference, Kisarazu, Japan, (June 1999).

A. K. Dunn, NMR Center, Massachusetts General Hospital, Harvard Medical School, Charlestown, Mass. 02129 (private communication, 2000).

S. Gaalema, Black Forest Engineering, Colorado Springs, Colo. (private communication, 2000).

J. T. Rantala, R. Levy, L. Kivimäki, and M. R. Descour, "Direct UV patterning of thick hybrid glass films for micro-opto-mechanical structures," *Electronics Letters*, 16, No. 6, pp. 530-531 (Mar. 16, 2000).

ANSYS is a product of ANSYS, Inc., Canonsburg, Pa. 15317 (www.ansys.com).

C. J. Wilson and P. A. Beck, "Fracture testing of bulk silicon microcantilever beams subjected to a side load", *Journal of Microelectromechanical Systems*, 5, No. 3, pp. 142-150 (1996).

R. R. Shannon, *The Art and Science of Optical Design*, Ch. 6, p. 361 (Cambridge University Press, 1997).

K. Sokolov, J. Galvan, A. Myakov, A. Lacy, R. Lotan, R. Richards-Kortum, "Realistic Three Dimensional Epithelial Tissue Phantoms for Biomedical Optics," submitted, *The Journal of Biomedical Optics* (2001).

P. Äyräs, J. T. Rantala, R. Levy, M. R. Descour, S. Honkanen, and N. Peyghambarian, "Multilevel structures in sol-gel thin films with a single UV-exposure using a gray-scale mask," *Thin Solid Films* 352, 9 (1999).

J. T. Rantala, P. Äyräs, R. Levy, S. Honkanen, M. R. Descour, N. Peyghambarian, "Binary phase zone-plate arrays based on hybrid sol-gel glass," *Optics Letters*, 23, 1939 (Dec. 15, 1998).

J. T. Rantala, GuideOptics, Inc., San Jose, Calif., and Espoo, Finland (private communication, 2000).

T. Christenson, Sandia National Laboratories, Albuquerque, N. Mex. (private communication, 2000).

F. Laermer and A. Schilp, "Method of anisotropically etching silicon," U.S. Pat. No. 5,501,893 (Mar. 26, 1996).

T. Collier, P. Shen, B. de Pradier, K. Sung, A. Malpica, M. Follen, R. Richards-Kortum, "Near real time confocal microscopy of amelanotic tissue: Dynamics of aceto-whitening enable nuclear segmentation," *Optics Express*, 6:40-48, 2000.

J. Mourant, J. Freyer, A. Hielscher, A. Eick, D. Shen, and T. Johnson, "Mechanisms of Light Scattering from Biological Cells Relevant to Noninvasive Optical-Tissue Diagnostics," Applied Optics, Vol. 37, 3585-3593, 1998.

H. W. Wang, J. Willis, M. I. Canto, M. V. Sivak, Jr., J. A. Izatt, "Quantitative Laser Scanning Confocal Autofluorescence Microscopy of Normal, Premalignant and Malignant Colonic Tissues," IEEE Trans BME, 46(19):1246-52 (1999).

C. L. Smithpeter, A. K. Dunn, A. J. Welch, R. R. Richards-Kortum, "Penetration Depth Limits of in vivo Confocal Reflectance Imaging," *Applied Optics*, 37:2749-54 (1998).

1999 *TLVs and BEIs*, published by ACGIH, Cincinnati, Ohio, p. 154.

R. K. Kimmel and R. E. Parks, eds., "Surface Texture," Ch. 8 in *ISO* 10110 *Optics and Optical Instruments*, Optical Society of America (1995).

L. Coghlan, U. Utzinger, R. Richards-Kortum, C. Brookner, A. Zuluaga, I. Gimeniz-Conti, M. Follen, "Fluorescence Spectroscopy of Epithelial Tissue Throughout the Dysplasia-Carcinoma Sequence in an Animal Model: Spectroscopic Changes Precede Morphologic Changes," in press, *Lasers in Surgery and Medicine* (2001).

G. M. Morris and K. J. McIntyre, "Optical system design with diffractive optics," in *Diffractive Optics for Industrial and Commercial Applications*, J. Turunen and F. Wyrowski, eds., Ch. 3, p. 95 (Akademie Verlag, 1997).

C. Brookner, M. Follen, I. Boiko, J. Galvan, S. Thomsen, A. Malpica, S. Suzuki, R. Lotan, R. Richards-Kortum, "Tissue Slices Autofluorescence Patterns in Fresh Cervical Tissue," *Photochemistry and Photobiology*, 71:730-36, 2000.

R. Drezek, C. Brookner, I. Pavlova, I. Boiko, A. Malpica, R. Lotan, M. Follen, R. Richards-Kortum, "Autofluorescence Microscopy of Fresh Cervical Tissue Sections Reveals Alterations in Tissue Biochemistry with Dysplasia," in press, *Photochemistry and Photobiology*, 2000.

G. S. Kino, "Intermediate Optics in Nipkow Disk Microscopes," in *Handbook of Biological Confocal Microscopy*, J. B. Pawley, ed., Ch. 10 (Plenum Press, 1995).

F. R. Miller, D. McEachern, and B. E. Miller, "Growth Regulation of Mouse Mammary Tumor Cells in Collagen Gel Cultures by Diffusible Factors Produced by Normal Mammary Gland Epithelium and Stromal Fibroblasts," *Cancer Research*, 49, pp. 6091-6097 (1989).

What is claimed is:

1. An apparatus for receiving and positioning optical components, the apparatus comprising:

a substrate;

one or more mounting slots formed in the substrate, each mounting slot comprising a mounting slot wall, and at least one of the mounting slots adapted to receive an optical component; and one or more springs, wherein at least one of the mounting slots is coupled to one of the springs, and wherein each spring comprises a first elongated portion and a second elongated portion, the second elongated portion coupled to the first elongated portion such that an angle defined by the first elongated portion and the second elongated portion is acute.

2. A multi-modal imaging apparatus for detecting and imaging pre-cancer, the apparatus comprising:

a substrate;

one or more mounting slots formed in the substrate, each mounting slot comprising a mounting slot wall, and at least one of the mounting slots adapted to receive an optical component;

one or more springs, wherein at least one of the mounting slots is coupled to one of the springs, and wherein each spring comprises a first elongated portion and a second elongated portion, the second elongated portion coupled to the first elongated portion such that an angle defined by the first elongated portion and the second elongated portion is acute;

a plurality of optical components configured to be contained at least partially in the mounting slots and held at least partially by the springs; and an illumination source;

wherein the light source and the optical components are configured for multi-modal imaging comprising at least autofluorescence imaging and reflectance imaging for detecting and imaging pre-cancer.

3. The apparatus of claim 2, wherein the multi-modal imaging comprises confocal imaging.

4. The apparatus of claim 2, wherein the multi-modal imaging comprises optical sectioning.

5. The apparatus of claim 4, further comprising a continually oscillating amplitude grating and wherein the multi-modal imaging comprises optical sectioning using the grating.

6. The apparatus of claim 2, wherein the substrate comprises silicon.

7. The apparatus of claim 2, wherein at least one of the mounting slots comprises one or more grooves formed in the mounting slot wall, each groove being adapted to receive a protrusion formed on the optical component.

8. The apparatus of claim 7, wherein the springs are configured to secure at least one of the protrusions formed on the optical component in at least one of the grooves formed in the mounting slot wall.

9. The apparatus of claim 8, wherein the optical components comprise:
   a detector configured to collect radiation from a sample;
   a beam splitter in operative relation with the illumination source and the detector, the beam splitter configured to select a first wavelength to be directed from the illumination source to the sample and configured to select a second wavelength to be directed from the sample to the detector; and
   a lens in operative relation with the beam splitter.

10. The apparatus of claim 9, wherein the optical components further comprise:
    a collector mirror in operative relation with the illumination source;
    one or more refractive lenses in operative relation with the beam splitter;
    a scanning grating in operative relation with the beam splitter, the scanning grating configured for optical sectioning; and
    a CMOS active-pixel image sensor.

11. The apparatus of claim 10, wherein the illumination source, detector, and beam splitter each comprise one or more protrusions that are adapted to be received in the one or more grooves.

12. The apparatus of claim 10, wherein the scanning grating comprises a double-pass scanning grating.

13. The apparatus of claim 10, wherein the scanning grating is integral with the substrate.

14. The apparatus of claim 2, wherein the illumination source emits one or more wavelengths of light optimized for distinguishing a pre-cancerous sample from a normal sample.

15. The apparatus of claim 2, wherein the illumination source emits wavelengths from between 350 nm to 500 nm.

16. The apparatus of claim 2, wherein the illumination source emits wavelengths from between 600 nm to 1100 nm.

17. The apparatus of claim 2, further comprising a low-magnification imaging system.

* * * * *